Figure 1:
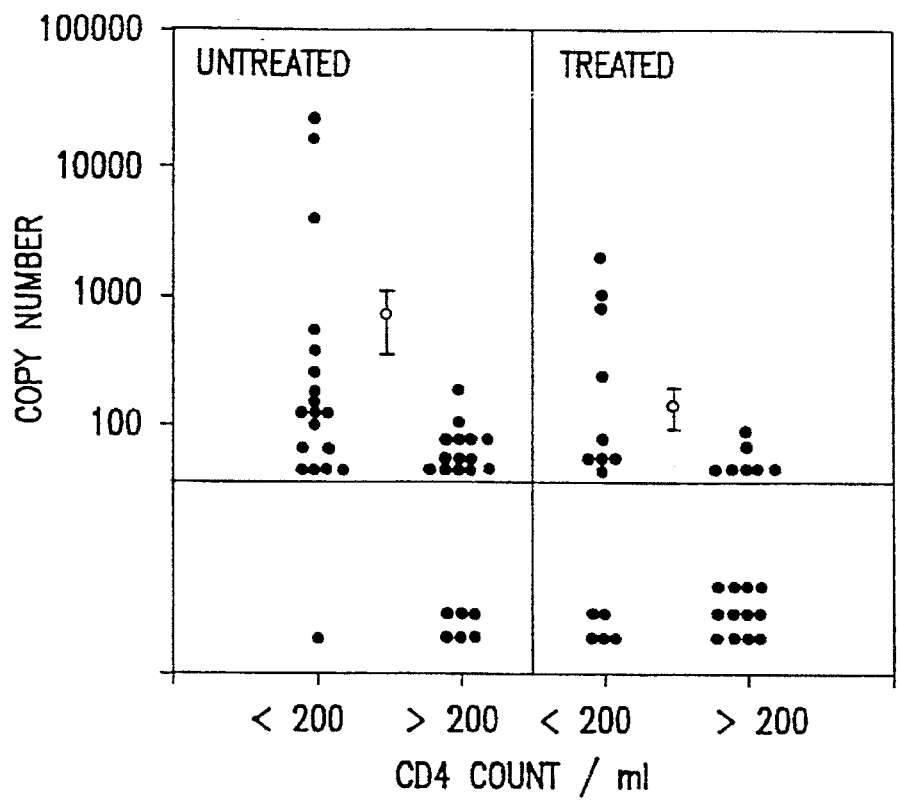

United States Patent [19]
Kozal et al.

[11] Patent Number: 5,650,268
[45] Date of Patent: Jul. 22, 1997

[54] POLYMERASE CHAIN REACTION ASSAYS FOR MONITORING ANTIVIRAL THERAPY AND MAKING THERAPEUTIC DECISIONS IN THE TREATMENT OF ACQUIRED IMMUNODEFICIENCY SYNDROME

[75] Inventors: Michael J. Kozal, Menlo Park; Thomas C. Merigan, Portola Valley, both of Calif.

[73] Assignee: Leland Stanford Junior University, Palo Alto, Calif.

[21] Appl. No.: 471,072

[22] Filed: Jun. 6, 1995

Related U.S. Application Data

[63] Continuation of Ser. No. 883,327, May 14, 1992, abandoned.

[51] Int. Cl.$^6$ .................................................. C12Q 1/68
[52] U.S. Cl. .............................. 435/5; 435/6; 436/601; 436/63; 514/2; 514/44; 536/23.1; 536/24.1; 536/24.3; 536/24.31; 536/24.32; 536/24.33; 935/77; 935/78
[58] Field of Search .................. 435/5, 6; 436/501, 436/63; 514/2, 44; 536/23.1, 24.1, 24.3–24.33; 935/77, 78

[56] References Cited

U.S. PATENT DOCUMENTS

| | | | |
|---|---|---|---|
| 4,683,195 | 7/1987 | Mullis et al. | 435/6 |
| 5,008,182 | 4/1991 | Sninsky et al. | 435/5 |

FOREIGN PATENT DOCUMENTS

| | | |
|---|---|---|
| 0-422-762-A2 | 4/1991 | European Pat. Off. . |
| 60828/90 | 2/1991 | United Kingdom . |

OTHER PUBLICATIONS

Chomczynski et al., 1987, "Single–Step Method of RNA Isolation by Acid Guanidinium Thiocyanate–Phenol–Chloroform Extraction" *Anal. Biochem.* 162:156–159.

Ehrnst et al., 1988, "Efficient Isolation of HIV From Plasma During Different Stages of HIV Infection" *J. Med. Virol.* 26:23–32.

Hewlett et al., 1988, "Detection in Plasma of HIV–1 Specific DNA and RNA by Polymerase Chain Reaction Before and After Seroconversion" *J. Clin. Immunoassay* 11:161–164.

Coombs et al., 1989, "Plasma Viremia in Human Immunodeficiency Virus Infection" *N. Engl. J. Med.* 321:1626–31.

Ho et al., 1989, "Quantitation of Human Immunodeficiency Virus Type 1 in the Blood of Infected Persons" *N. Engl. J. Med.* 321:1621–1625.

Larder et al., 1989, "HIV with Reduced Sensitivity to Zidovudine (AZT) Isolated During Prolonged Therapy" *Science* 243:1731–1734.

Larder et al., 1989, "Multiple Mutations in HIV–1 Reverse Transcriptase Confer High–Level Resistance to Zidovudine (AZT)" *Science* 246:1155–1158.

Meyerhans et al., 1989, "Temporal Fluctuations in HIV Quasispecies In Vivo Are Not Reflected by Sequential HIV Isolations" *Cell* 58:901–910.

Rooke et al., 1989, "Isolation of Drug–Resistant Variants of HIV–1 From Patients on Long–Term Zidovudine Therapy" *AIDS* 3:411–415.

(List continued on next page.)

*Primary Examiner*—Stephanie W. Zitomer
*Assistant Examiner*—Ardin H. Marschel
*Attorney, Agent, or Firm*—Laura A. Coruzzi; Pennie & Edmonds

[57] ABSTRACT

The present invention relates to methods of monitoring, via polymerase chain reaction, the clinical progression of human immunodeficiency virus infection and its response to antiretroviral therapy. According to the invention, polymerase chain reaction assays may be used to predict immunological decline and to identify, at an early stage, patients whose infection has become resistant to a particular antiretroviral drug regimen.

10 Claims, 9 Drawing Sheets

|  | SERUM | |
|---|---|---|
|  | WILDTYPE | MUTANT |
| PBMC WILDTYPE | 11 | 10 |
| PBMC MUTANT | 0 | 17 |

OTHER PUBLICATIONS

Tersmette et al., 1989, "Association Between Biological Properties of Human Immunodeficiency Virus Variants and Risk for AIDS and AIDS Mortality" *Lancet* 1:983–985.

Aoki et al., 1990, "Quantitative Analysis of HIV–1 Proviral DNA in Peripheral Blood Mononuclear Cells from Patients with AIDS or ARC: Decrease of Proviral DNA Content Following Treatment with 2', 3'–Dideoxyinosine (ddI)" *AIDS Res. Hum. Retroviruses* 6:1331–1339.

Boucher et al., 1990, "Zidovudine Sensitivity of Human Immunodeficiency Viruses From High–Risk Symptom–Free Individuals During Therapy" *Lancet* 336:585–590.

Coyle et al., 1990, "Detection of Human Immunodeficiency Virus in Plasma by RNA Directed Polymerase Chain Reaction in a Cohort of Hemophiliacs" *Clin. Res.* 38:778a (Abstr.).

Fischl et al., 1990, "A Randomized Controlled Trial of a Reduced Daily Dose of Zidovudine in Patients with the Acquired Immunodeficiency Syndrome" *N. Engl. J. Med.* 323:1009–1014.

Karpas et al., 1990, "Polymerase Chain Reaction Evidence for Human Immunodeficiency Virus 1 Neutralization by Passive Immunization in Patients With AIDS and AIDS–related Complex" *Proc. Natl. Acad. Sci. USA* 87:7613–7617.

Kawasaki, 1990, "In PCR Protocals: A Guide to Methods and Applications" pp. 21–27, M. A. Innis, D. H. Gelfand, J. J. Sninsky, and T. J. White, eds. Academic Press, Berkeley, California.

Kellog et al., 1990, "In PCR Protocols: A Guide to Methods and Applications" pp. 337–347, M. A. Innis, D. H. Gelfand, J. J. Sninsky, and T. J. White, eds. Academic Press, Berkeley, California.

Land et al., 1990, "Decreased In Vitro Susceptibility to Zidovudine of HIV Isolates Obtained from Patients with AIDS" *J. Infect. Dis.* 161:326–329.

Levenson et al, 1990, "In PCR Protocols: A Guide to Methods and Applications" pp. 99–112, M. A. Innis, D. H. Gelfand, J. J. Sninsky, and T. J. White, eds. Academic Press, Berkeley, California.

Richman et al., 1990, "Effect of Stage of Disease and Drug Dose on Zidovudine Susceptibilities of Isolates of Human Immunodeficiency Virus" *J. AIDS* 3:743–746.

Volberding et al., 1990, "Zidovudine in Asymptomatic Human Immunodeficiency Virus Infection" *N. Engl. J. Med.* 322:941–949.

Bagnarelli et al., 1991, "Detection of Human Immunodeficiency Virus Type 1 Genomic RNA in Plasma Samples by Reverse–Transcription Polymerase Chain Reaction" *J. Med. Virol.* 34:89–95.

Daar et al., 1991, "Transient High Levels of Viremia in Patients with Primary Human Immunodeficiency Virus Type 1 Infection" *N. Engl. J. Med.* 324:961–964.

Escaich et al., 1991, "Plasma Viraemia as a Marker of Viral Replication in HIV–Infected Individuals" *AIDS* 5:1189–1193.

Holodniy et al., 1991, "Inhibition of Human Immunodeficiency Virus Gene Amplification by Heparin" *J. Clin. Microbiol.* 29:676:679.

Holodniy et al., 1991, "Detection and Quantification of Human Immunodeficiency Virus RNA in Patient Serum by Use of the Polymerase Chain Reaction" *J. Infect. Dis.* 163:862–866.

Holodniy et al., 1991, "Reduction in Plasma Human Immunodeficiency Virus Ribonucleic Acid after Dideoxynucleoside Therapy as Determined by the Polymerase Chain Reaction" *J. Clin. Invest.* 88:1755–1759.

Japour et al., 1991, "Detection of Human Immunodeficiency Virus Type 1 Clinical Isolates With Reduced Sensitivity to Zidovudine and Dideoxyinosine by RNA–RNA Hybridization" *Proc. Natl. Acad. Sci. USA* 88:3092–3096.

Larder et al., 1991, "Zidovudine Resistance Predicted by Direct Detection of Mutations in DNA From HIV–Infected Lymphocytes" *AIDS* 5:137–144.

McElrath et al., 1991, "Latent HIV–1 Infection in Enriched Populations of Blood Monocytes and T Cells from Seropositive Patients" *J. Clin. Invest.* 87:27–30.

Ottman et al., 1991, "The Polymerase Chain Reaction for the Detection of HIV–1 Genomic RNA in Plasma From Infected Individuals" *J. Virol Methods* 31:273–284.

Richman et al., 1991, "Detection of Mutations Associated with Zidovudine Resistance in Human Immunodeficiency Virus by Use of the Polymerase Chain Reaction" *J. Infect. Dis.* 164:1075–1081.

Semple et al., 1991, "Direct Measurement of Viraemia in Patients Infected With HIV–1 and Its Relationship to Disease Progression and Zidovudine Therapy" *J. Virol. Methods* 35:38–45.

St Clair et al., 1991 "Resistance to ddI and Sensitivity to AZT Inducted by a Mutation in HIV–1 Reverse Transcriptase" *Science* 253:1557–1559.

Boucher et al., 1992, "Ordered Appearance of Zidovudine Resistance Mutations During Treatment of 18 Human Immunodeficiency Virus–Positive Subjects" *J. Infect. Dis.* 165:105–110.

Bush et al., 1992, "Detection of Human Immunodeficiency Virus Type 1 RNA in Plasma Samples from High–Risk Pediatric Patients by Using the Self–Sustained Sequence Replication Reaction" *J. Clin Microbiology* 30(2):281–286.

Henrard et al., 1992, "A Sensitive Viral Capture Assay for Detection of Plasma viremia in HIV–Infected Individuals" *AIDS Res. Hum. Retroviruses* 8:47–52.

Kellam et al., 1992, "Fifth Mutation in Human Immunodeficiency Virus Type 1 Reverse Transcriptase Contributes to the Development of High–Level Resistance to Zidovudine" *Proc. Natl. Acad. Sci. USA* 89:1934–1938.

Kusumi et al., 1992, "Human Immunodeficiency Virus Type 1 Envelope Gene Structure and Diversity In Vivo and After Cocultivation In Vitro" *J. Virol. Methods* 66:875–885.

Tudor–Williams et al., 1992, "HIV–1 Sensitivity to Zidovudine and Clinical Outcome in Children" *Lancet* 339:15–19.

Yerly et al., 1992, "Quantitaion of Human Immunodeficiency Virus Provirus and Circulating Virus: Relationship with Immunologic Parameters" *J. Infect. Dis.* 166:269–76.

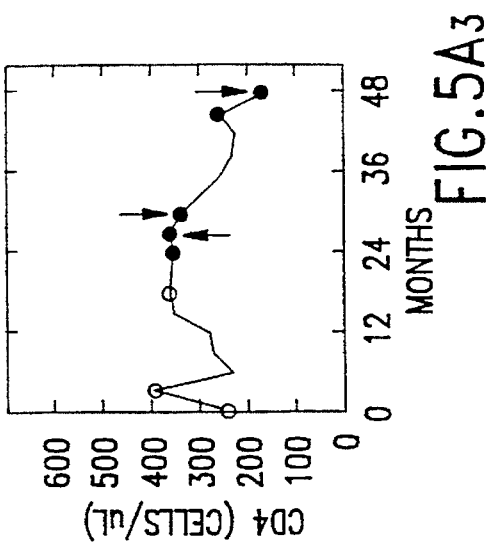
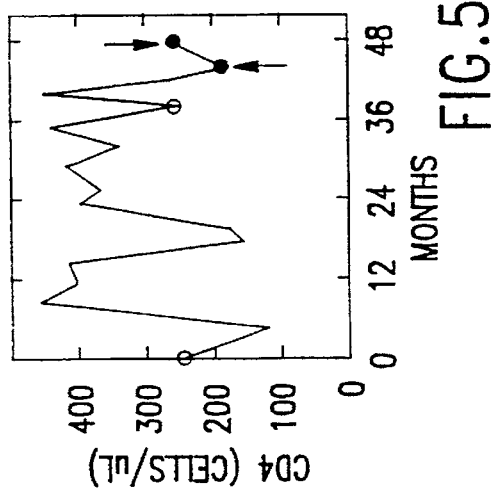
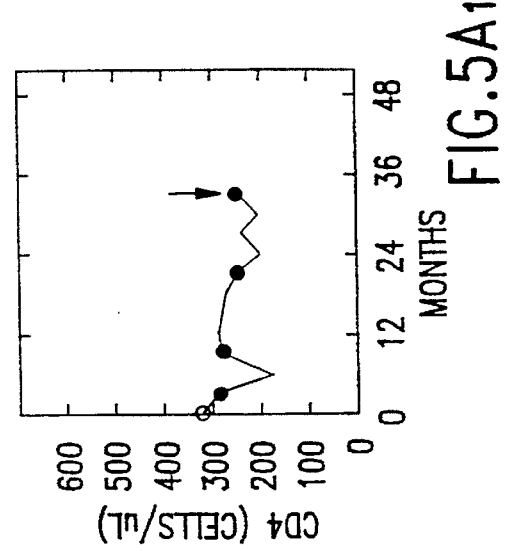
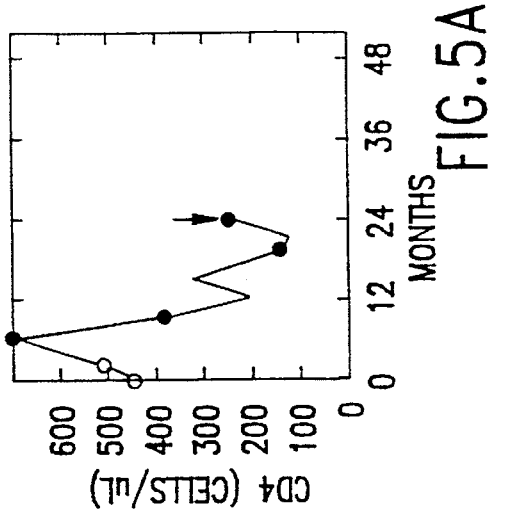
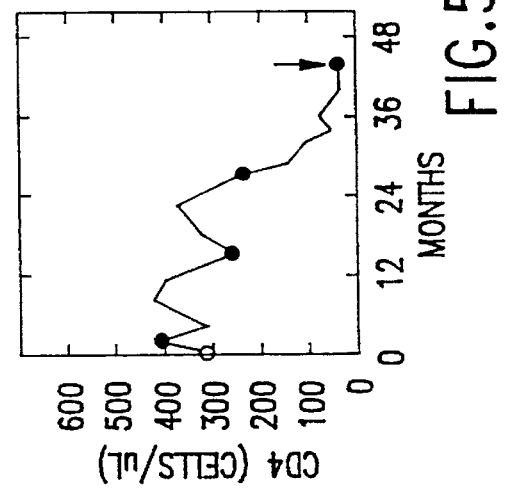
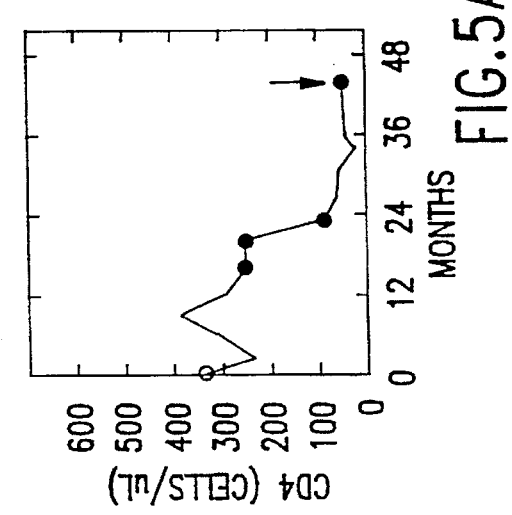

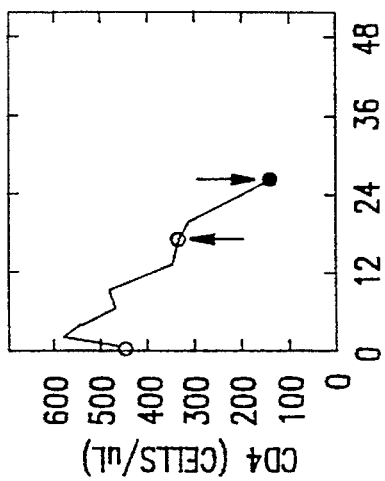
FIG.5A7
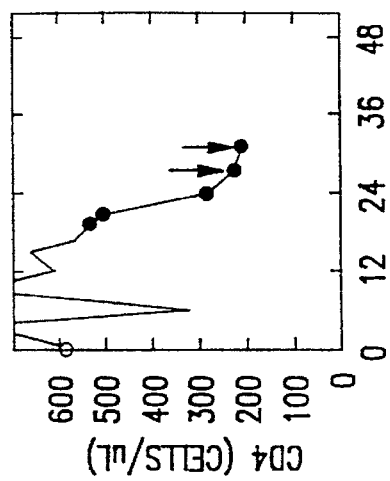
FIG.5A8
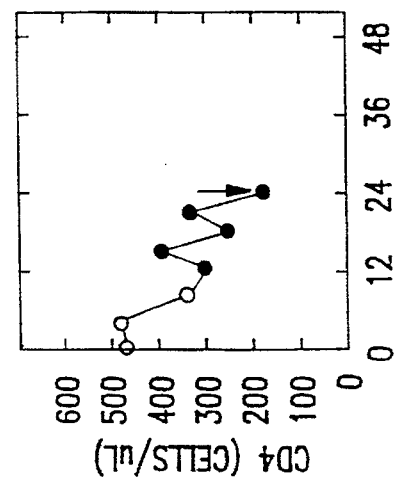
FIG.5A9
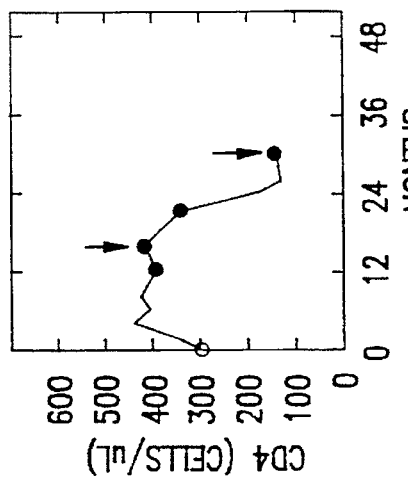
FIG.5A10
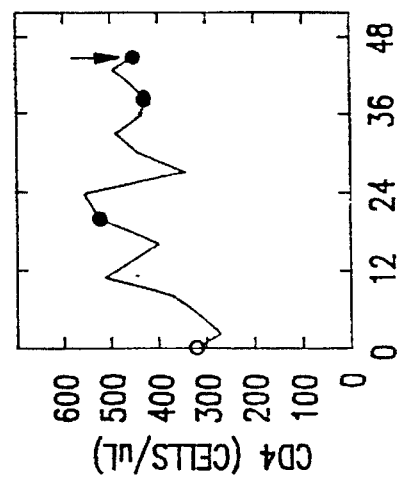
FIG.5A11
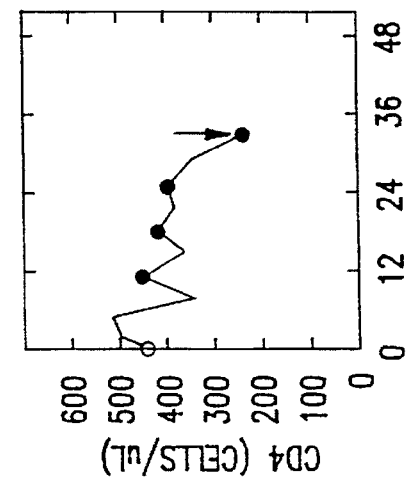
FIG.5A12

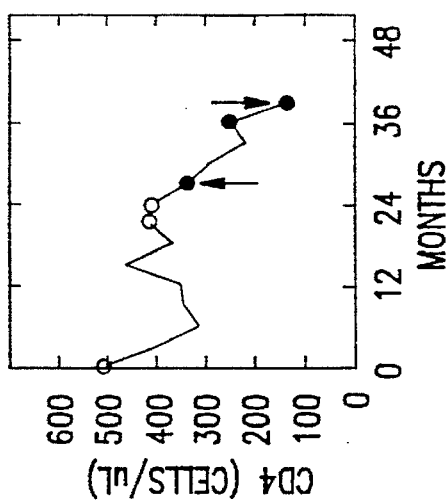
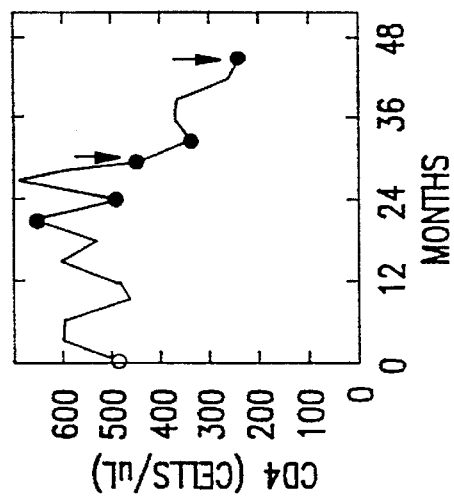
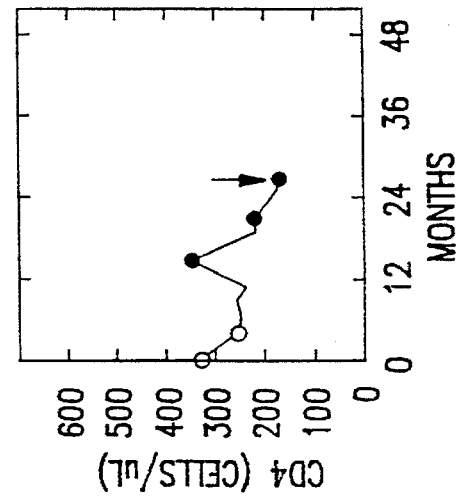
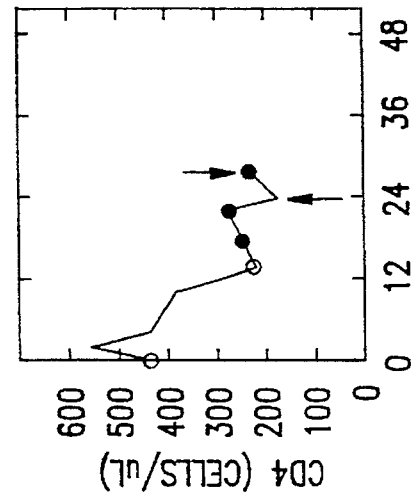

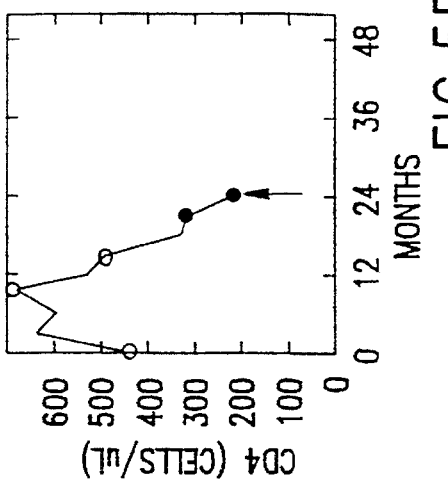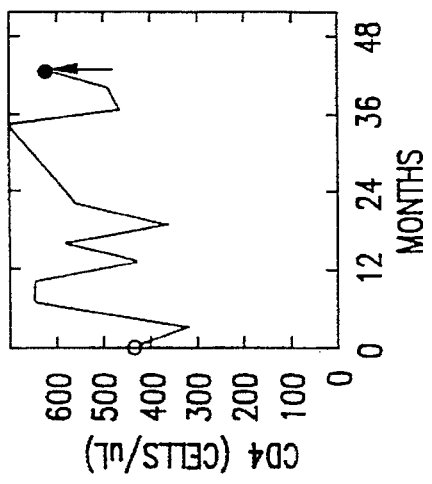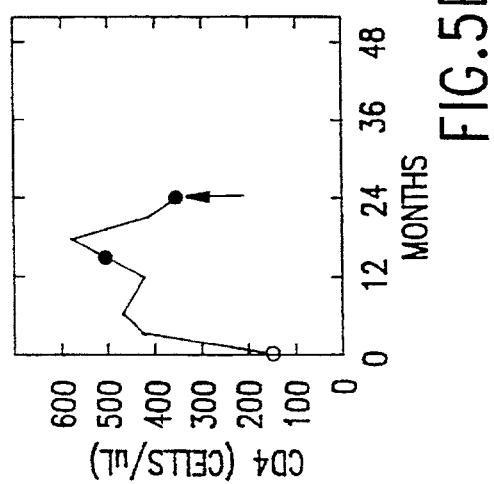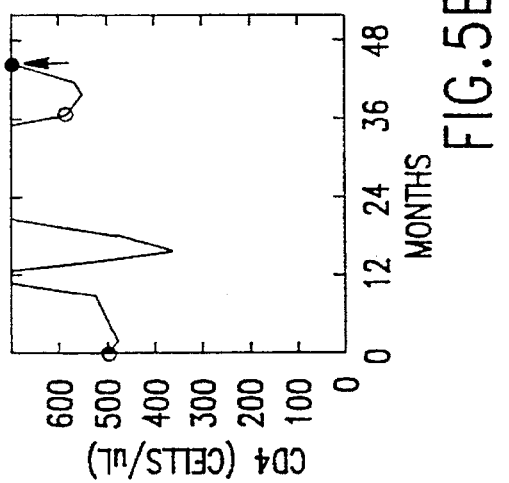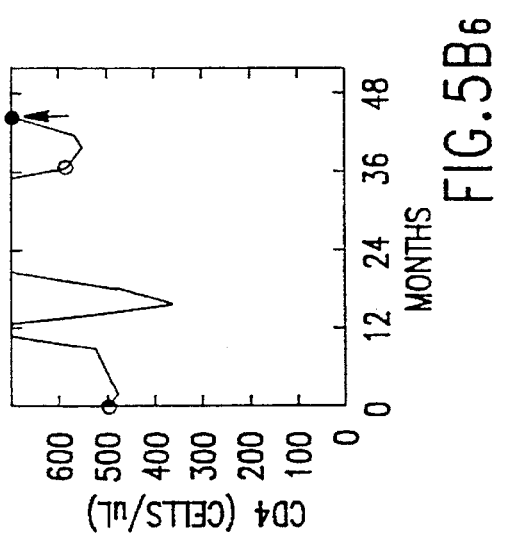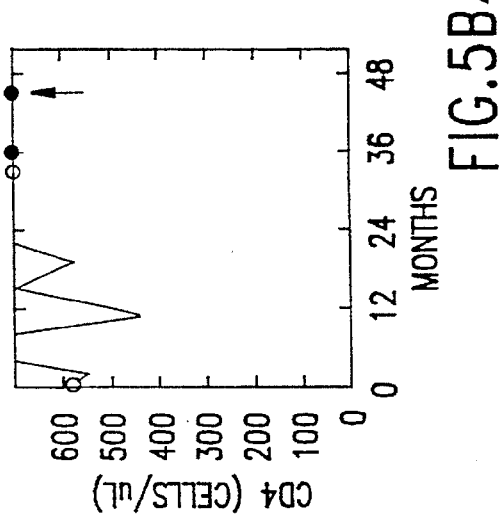

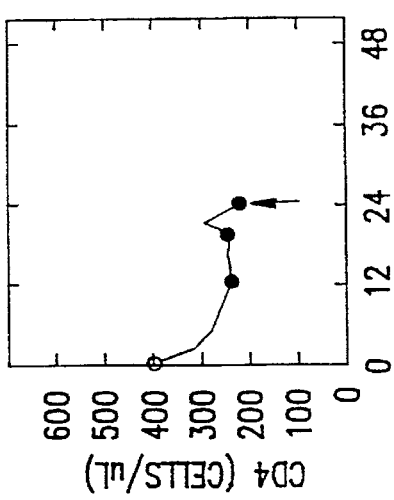
FIG.5B9
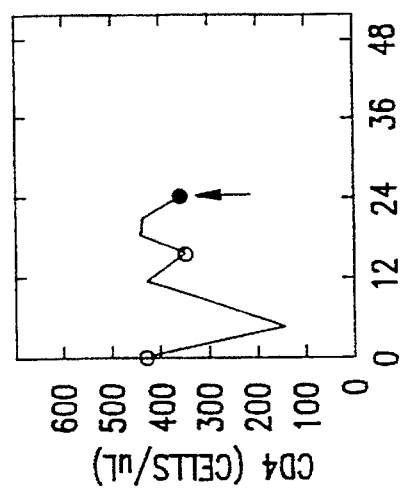
FIG.5B8
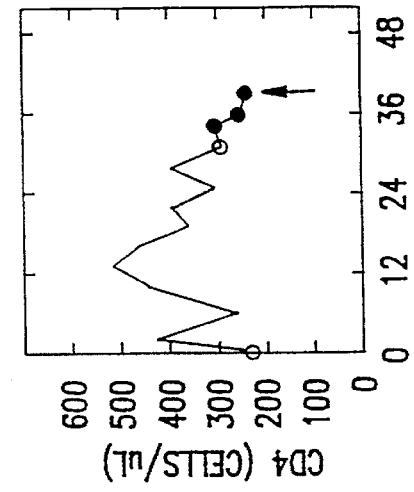
FIG.5B7
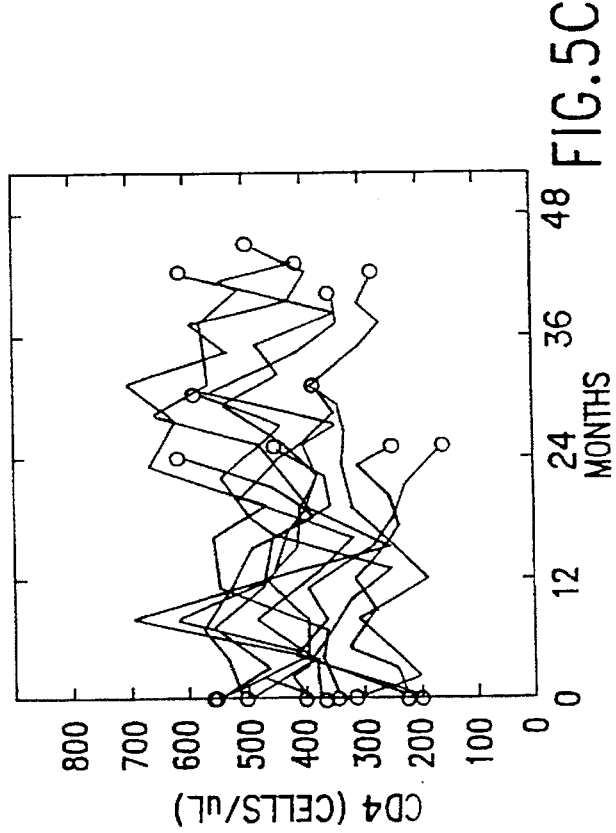
FIG.5C
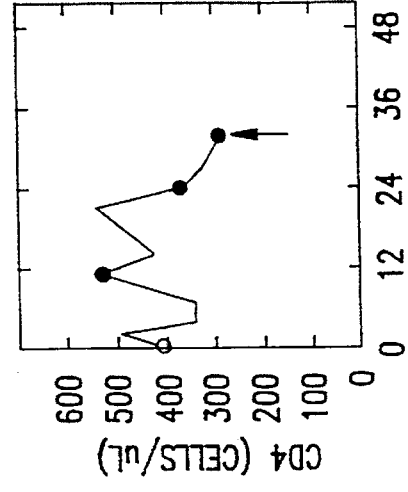
FIG.5B10

SERUM

|  | WILDTYPE | MUTANT |
|---|---|---|
| PBMC WILDTYPE | 11 | 10 |
| PBMC MUTANT | 0 | 17 |

FIG.6

HIV 1 gag (p24) CORE PROTEIN

| NAME | OLIGO 1 |
|---|---|
| SK 38 | 5'-ATA ATC CAC CTA TCC CAG TAG GAG AAAT |

| | OLIGO 2 |
|---|---|
| SK 39 | 5'-TTT GGT CCT TGT CTT ATG TCC AGA ATG C |

| | PROBE |
|---|---|
| SK 19 | 5'-ATC CTG GGA TTA AAT AAA ATA GTA AGA ATG TAT AGC CCT AC |

FIG.7

POLYMERASE CHAIN REACTION ASSAYS FOR MONITORING ANTIVIRAL THERAPY AND MAKING THERAPEUTIC DECISIONS IN THE TREATMENT OF ACQUIRED IMMUNODEFICIENCY SYNDROME

This application is a continuation application of U.S. application Ser. No. 07/883,327, filed May 14, 1992, now abandoned, which is incorporated herein by reference in its entirety.

This invention was made with Government support under contracts AI27762-04 and AI27666-07 awarded by the National Institutes of Health. The Government has certain rights in this invention.

1. INTRODUCTION

The present invention relates to methods of monitoring, via polymerase chain reaction, the clinical progression of human immunodeficiency virus infection and its response to antiretroviral therapy. According to the invention, polymerase chain reaction assays may be used to predict immunological decline and to identify, at an early stage, patients whose infection has become resistant to a particular antiretroviral drug regimen.

2. BACKGROUND OF THE INVENTION

Human immunodeficiency virus (HIV) isolated from patients treated with zidovudine (AZT) may demonstrate markedly reduced in vitro susceptibility to AZT (Larder et al., 1989, Science 243:1731–1734; Rooke et al., 1989, AIDS 3:411–415; Land et al., 1990, J. Infect. Dis. 161:326–329; Boucher et al., 1990, Lancet 336:585–590; Japour et al., 1991, Proc. Natl Acad. Sci. 88:3092–96; Tudor-Williams et al., 1992, Lancet 339:15–19). This reduced susceptibility has been related to the duration of therapy with AZT and the severity of HIV disease at the time AZT therapy is begun (Richman et al., 1990, J. AIDS 3:743–756). Nucleotide sequence analysis of AZT-resistant HIV strains has revealed a number of mutations in the reverse transcriptase (RT) gene associated with decreased AZT susceptibility (Larder et al., 1989, Science 246:1155–1158; Larder et al., 1991, AIDS 5:137–144; Kellam et al., 1992, Proc. Natl. Acad. Sci. USA 89:1934–1938; St. Clair et al., 1991, Science 253:1557–1559; Richman et al., 1991, J. Infect. Dis. 164:1075–1081). Molecular cloning experiments have confirmed that these mutations in the RT gene confer AZT resistance (Larder et al., 1989, Science 246:1155–1158; Larder et al., 1991, AIDS 5:137–144; Kellam et al., 1992, Proc. Natl. Acad. Sci. USA 89:1934–1938; St. Clair et al., 1991, Science 253:1557–1559). Of these mutations the one at codon 215 resulting in a single amino acid substitution (Thr→Tyr or Phe) has been shown to be the most common mutation and to have the greatest impact on in vitro susceptibility to AZT (Larder et al., 1991, AIDS 5:137–144; Richman et al., 1991, J. Infect. Dis. 164:1075–1081; Boucher et al., 1992, J. Inf. Dis.,165:105–110).

Several studies have addressed the relationship between in vitro AZT resistance, mutations in the RT gene and clinical disease. Richman and coworkers studied 32 patients with different stages of HIV disease and demonstrated that the development of in vitro AZT resistance was related to the duration of therapy with AZT and to the severity of disease at the time AZT was begun (Richman et al., 1990, J.AIDS 3:743–746). Boucher and coworkers studied HIV P24-antigenemic patients treated with AZT for 2 years. They observed that at 6 months, seven patients with a mutation at codon 215 had a weak, non-statistically significant trend toward lower CD4 counts compared to nine patients who were wild type at codon 215 (Boucher et al., 1990, Lancet 336:585–590). After 2 years nearly all patents had the mutation. Tudor-Williams and coworkers studied HIV isolates from 19 symptomatic children treated with AZT for 9–39 months and showed that in vitro AZT resistance was associated with poor clinical outcome (Tudor-Williams et al., 1992, Lancet 339:15–19). However, adult studies have not shown a precise correlation between the development of in vitro resistance and progression of HIV disease.

3. SUMMARY OF THE INVENTION

The present invention relates to methods of monitoring, via polymerase chain reaction (PCR), the clinical progression of human immunodeficiency virus (HIV) infection and its response to antiviral therapy. It is based, in part, on the discovery that plasma HIV RNA copy number, as measured using PCR, may be used as a sensitive marker of the circulating HIV viral load to assess the therapeutic effect of antiretroviral compounds. In working examples described herein, an increase in plasma HIV RNA copy number was found to correlate with disease progression, and successful antiretroviral therapy was found to correlate with a decline in plasma HIV RNA copy number.

The invention is also based, in part, on the discovery that genetic changes in HIV which confer resistance to antiretroviral therapy may be rapidly determined directly from patient peripheral blood mononuclear cells (PBMC) and/or plasma HIV RNA using a "nested" PCR procedure. In working examples disclosed herein, a mutation at codon 215 of HIV reverse transcriptase (RT) was found to occur in AZT-treated patients which correlated with refractoriness to AZT treatment. The mutation was found in plasma HIV RNA one to eight months before it was detectable in PBMC. The development of the codon 215 mutation in HIV RT was found to be a harbinger of immunological decline, which occurred between six and twelve months after the mutation was detectable in plasma HIV RNA.

In particular embodiments of the invention, PCR assay may be used to monitor the clinical progression of HIV infection in patients receiving antiretroviral therapy. An increase in plasma HIV copy number detected by such an assay would correlate with refractoriness to treatment. If a patient being treated with an antiretroviral therapeutic agent exhibits an increase in plasma HIV RNA copy number, a physician should consider altering the patients treatment regimen. It should be noted that the present invention offers the advantage of being more sensitive in measuring HIV virus than standard methods which measure plasma p24 antigen or infectious virus detectable by culture techniques.

In further embodiments of the invention, PCR assay may be used to detect mutations at codon 215 of HIV RT which correlate with resistance to antiretroviral therapy and which precede immunologic decline by 6–12 months. Once mutation at codon 215 has been detected in a patient undergoing antiretroviral therapy, an alteration in the therapeutic regimen must be considered. The speed at which a modified regimen should be instituted may depend on whether the mutation is present in plasma HIV RNA or PBMC. If the mutation is present in PBMC, a rapid alteration in therapy may be warranted.

In patients suffering from HIV infection, opportunistic infections arising as a result of a compromised immune system can be rapidly fatal. It is therefore extremely important to strive to avoid deterioration of the immune system in these patients. Because the present invention enables the early prediction of immunological decline, it allows alteration of a patient's therapeutic regimen so as to avoid opportunistic infections, and therefore may be used to promote survival and improve the quality of life of HIV-infected patients.

4. DESCRIPTION OF THE FIGURES

FIG. 1. Human immunodeficiency virus RNA copy number in 200 µl of plasma from 72 subjects as determined by cDNA gene amplification. Of 39 patients who were not currently receiving antiretroviral therapy, 20 had a CD4 count<200/ mm$^3$ (HIV copy number 1,369±707) and 19 had a CD4 count>200/mm$^3$ (HIV copy number 44±10). Of 33 subjects who were currently on AZT, 14 had a CD4 count<200/ mm$^3$ (HIV copy number 295±5) and 19 had a CD4 count>200/ mm$^3$ (HIV copy number 16±5). Mean copy number (open circles) of subjects not on therapy was 690±360 as compared to 134±219 for patients currently on AZT ($P<0.05$, independent sample t test).

Figure 2:
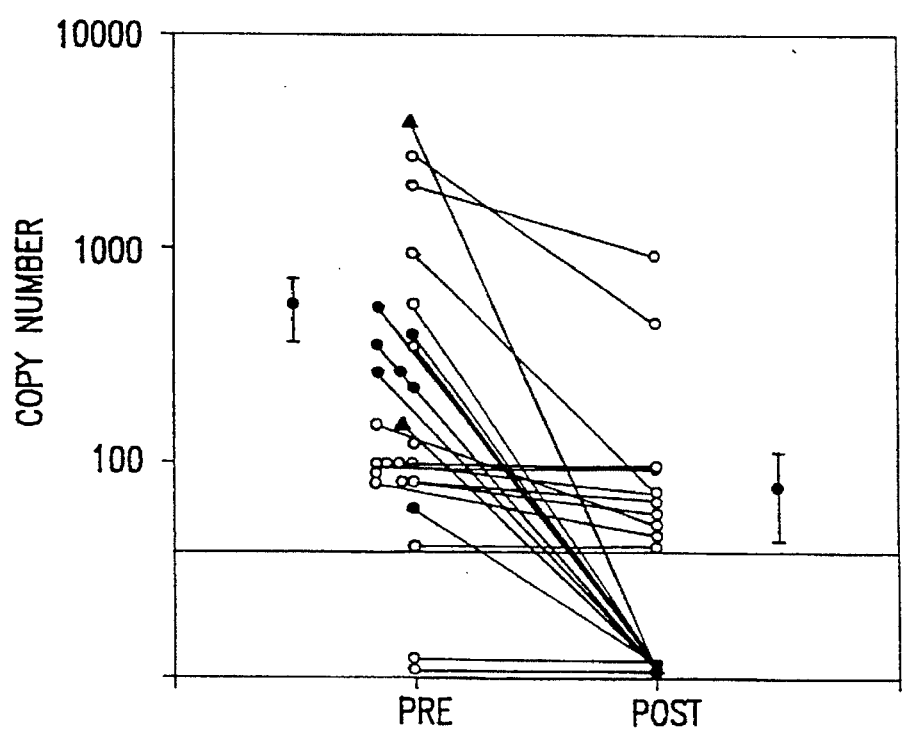

FIG. 2. Human immunodeficiency virus RNA copy number in plasma from 27 subjects before (pre) and 1 mo after (post) dideoxynucleoside therapy. (○) AZT; (●) AZT +ddI; and (▲) ddI alone. Mean copy number decreased from 540±175 to 77±35 after therapy ($P<0.05$ paired t test).

Figure 3:
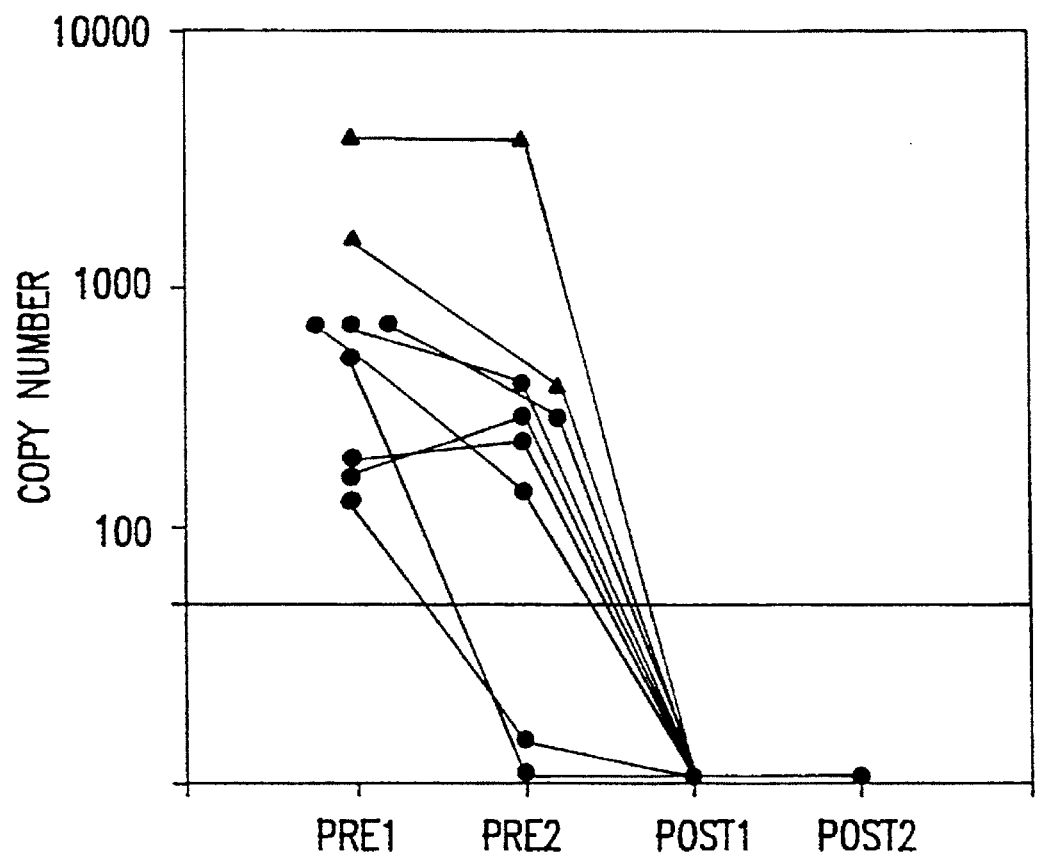

FIG. 3. Human immunodeficiency virus RNA copy number in plasma from 9 subjects with two samples obtained before initiation of therapy (pre 1 and pre 2) and two samples obtained 1 and 2 mo after commencing therapy (post 1 and post 2). (▲) ddI alone; (●) ddI +AZT.

Figure 4A:
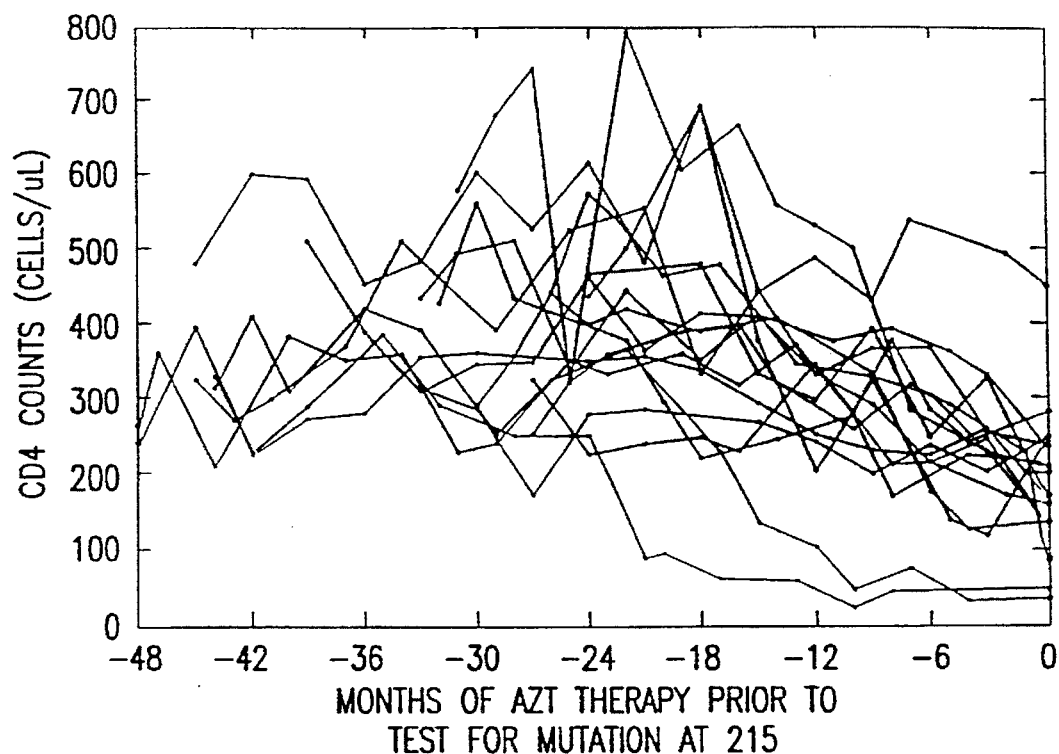
Figure 4B:
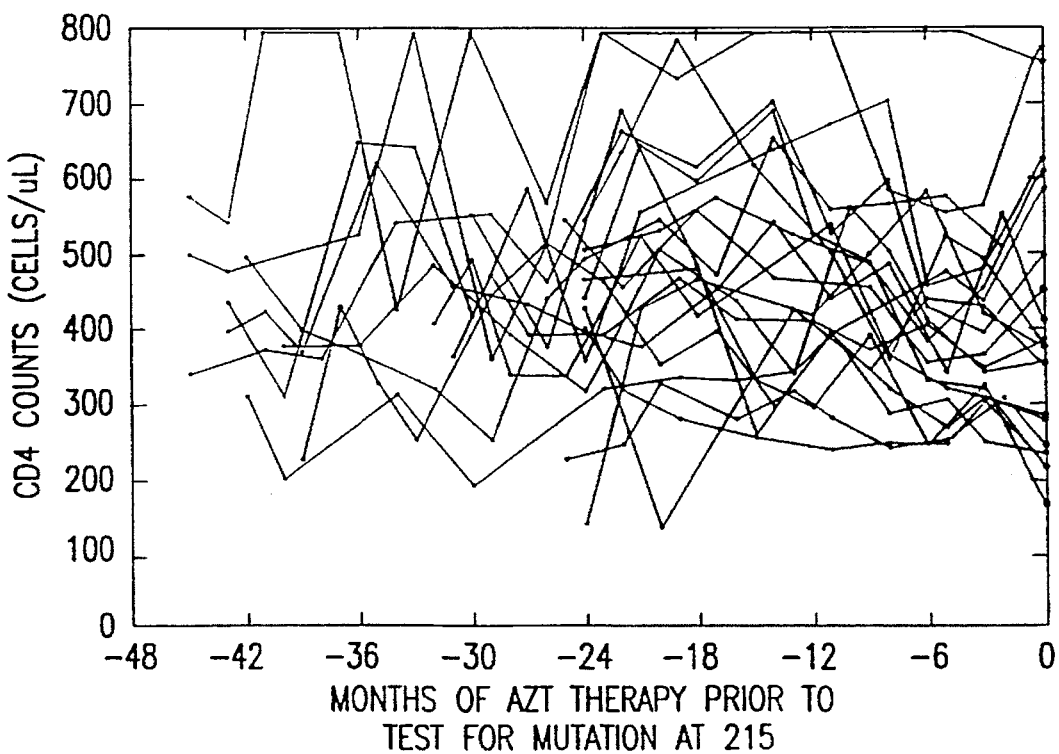

FIGS. 4A and 4B. Serial CD4 counts in PBMC (cells/µl) of 17 patients in which HIV reverse transcriptase carried a mutation at codon 215 (4A) and of 21 patients in which HIV reverse transcriptase was wild type at codon 215 4B.

FIG. 5A–5C. CD4 cell counts in PBMC from serial time points in 37 patients. ○= wild type sequence in serum specimen, ●=mutant sequence in serum, ↑=wild type sequence in PBMC, ↓=mutant sequence in PBMC; FIGS. 5A$_1$ to 5A$_{16}$ 16 patients mutant at codon 215 in both serum HIV RNA and PBMC (proviral DNA). FIGS 5B$_1$ to 5B$_{10}$ 10 patients mutant at codon 215 in serum HIV RNA but wild type in their PBMC. 5C: 11 patients whom remained wild type at codon 215 in their serum HIV RNA and PBMC.

FIG. 6. Relationship of PBMC to serum genotypes in the 38 patients at study endpoint.

FIG. 7. Nucleotide sequences of SK38, SK39, and SK19.

5. DETAILED DESCRIPTION OF THE INVENTION

The present invention relates to methods of monitoring, via PCR, the clinical progression of HIV infection in patients receiving antiretroviral therapy. For purposes of clarity and not by way of limitation, the detailed description of the invention is divided into the following subsections:

(i) PCR assay of plasma HIV RNA;

(ii) PCR assay of peripheral blood mononuclear cells;

(iii) PCR assay for mutation at codon 215 of HIV reverse transcriptase; and (iv) utility of the invention.

It should be noted that heparin appears to have an inhibitory effect on gene amplification via PCR. It is therefore desireable to avoid using heparin as an anticoagulant of patient blood samples. If herapin has been used in a sample, the sample may be purified of heparin, for example, by collecting virus by ultracentrifugation.

5.1 PCR ASSAY OF PLASMA HIV RNA

According to the invention, it is desireable to avoid degradation of RNA in plasma samples prior to measurement of HIV RNA copy number. Therefore, in preferred embodiments of the invention, guanidinium is added to plasma or serum samples prior to storage at a concentration of about 2.5M and samples are kept frozen at −70° C., with no samples stored for longer than about 3 months. Serum may be used interchangeably with plasma according to the invention.

RNA may be extracted from plasma using standard techniques, such as those set forth in Chomczynski and Sacchi, 1987, Ann. Biochem. 162:156–159. For example, 200 µl of clarified plasma to which 200 µl of 5M guanidinium thiocyanate had previously been added may be extracted with phenol/chloroform and precipitated with isopropanol. The resulting pellet may then be washed in 75 percent ethanol, dried, and brought up into solution in diethylpyrocarbonate-treated glass distilled water.

From plasma RNA, HIV RNA may be transcribed to cDNA using a suitable reverse transcriptase (for example, Moloney murine leukemia virus reverse transcriptase) using standard techiques, such as for example, those set forth in Kawasaki, 1990, in "PCR Protocols: A Guide to Methods and Applications," Innis et al., eds., Academic Press, Berkeley, CA. pp. 21–27. Any suitable primer for amplification of HIV genomic RNA sequences may be used, including, but not limited to, the oligomers SK38, SK39, and SK19 (FIG. 7) described in Kellog et al., 1990, in "PCR Protocols: A Guide To Methods and Applications," Innis et al., etds., Academic Press, Berkeley, Calif. pp. 337–347. In a preferred embodiment of the invention, HIV cDNA may be amplified as follows: to a 100 µl reaction mixture, cDNA prepared as described supra may be added, together with 50 pmol of primers SK38 and SK39, 10 mM of each dNTP, 10 mM Tris (pH 8.3), 2.5 mM MgCl$_2$,50 mM KCl, and 2.5 U of recombiTaq DNA polymerase (Perkin-Elmer Cetus, Norwalk, Conn.). The mixture may then be overlaid with 50 µl of mineral oil, and tubes containing the reaction may be placed in a DNA thermal cycler (e.g. Perkin-Elmer Cetus) for about 30 cycles of amplification with the following program: 95° C./30 seconds, 55° C./30 seconds, and 72° C./60 seconds for denaturation, annealing, and extension, respectively. Negative and positive controls which include both high and low copy number HIV RNA and DNA may be added at each step.

It is important that the number of cycles not exceed 35, and preferably, only about 30 cycles of amplification are used in the PCR. Using a greater number of cycles may detract from the sensivity of the assay.

The copy number of HIV RNA may then be measured by methods known to the skilled artisan. For example, the number of copies of HIV RNA in a patient Sample may be quantiated by hybridizing the product of the above PCR with a detectably labeled probe that is complementary to HIV sequence. The amount of signal generated by probe hybridized to PCR product may then be compared to the amount of signal generated by probe hybridized to a known copy number of HIV. Probe may be detectably labeled by an enzyme, a radioisotope, a fluorescent compound, a chromogenic compound, or any other detectably labeled compound.

In a preferred, nonlimiting embodiment of the invention, at least one of the PCR primers may be biotinylated, probe may be labeled with horseradish peroxidase (HRP), and copy number may be evaluated by an enzyme-linked affinity assay as follows. 96-well microplates (Maxisorp; Nunc, Naperville, Ill.) may be coated with 100 µl of a 0.1 mg/ml solution of avidin (Sigma Chemical Co., St. Louis, Mo.) in 50 mM Na$_2$CO$_3$ (pH 9.6) overnight at room temperature. Wells may then be washed twice with PBS, and then filled with 300 µl of a blocking solution containing 5× Denhardt's solution, 1% gelatin (Sigma), 250 µl/ml sheared herring sperm DNA (Promega Biotec, Madison, Wis.) at least overnight at 4° C. Immediately before use, the blocking solution may be aspirated from each well and 5 µl of PCR product prepared as described supra (using at least one biotinylated primer) may be added to each well together with 65 µl of a hybridization solution containing 5× saline sodium phosphate EDTA, 5× Denhardt's solution; and 1 pmol of HRP-labeled SK19 HIV gag-specific probe. Because HIV primer was biotinylated, HIV amplified sequences should selectively adhere to the avidin-coated wells, so that a capture and hybridization reaction may be carried out for 1 hour at 42° C. Each well may then be washed about 20 times with PBS containing 0.05% Tween-20, for example, using a Biomek™ 1000 Automated Workstation (Beckman Instruments, Inc., Palo Alto, Calif.). The HRP substrate 0-phenylenediamine (Sigma) may then be prepared at 0.6 mg/ml in 0.1M citrate buffer (pH 5.5) containing 0.03% hydrogen peroxide, and 150 µl of this solution may be added to each well. After about 10 minutes the reaction may be stopped with 1N H$_2$SO$_4$ and the optical density of each well measured at 490 nm, for example by the Biomek 1000. A lower level of positivity had been defined as an absorbance of 0.135. This cutoff value was calculated from the mean absorbance obtained from a group of seronegative samples plus three standard deviations. Copy number from subject samples may be determined from the absorbances obtained from a dilution series of an RNA gag gene construct of known copy number (Holodniy et al., 1991, J. Infect. Dis. 163:862–866).

In an alternate preferred, specific embodiment, RNA collected from plasma may be reverse-transcribed by using 500 ng of primer A (5'-TTCCCATTAGTCCTATT-3') (SEQ ID NO:1) and 5 units of MuLV RT (Bethesda Research Labs) in 10 µl of amplification buffer (25 mM kCL, 50 mM Tris HCl pH 8.3, 0.1 mg/ml bovine serum albumin, 1.45 mM each of dATP, dGTP, dCTP and dTTP, 1.5 mM MgCl$_2$, and 2.5 U of RNasin (Promega)) for 10 min. at room temperature, then 30 minutes at 42° C. followed by heat inactivation at 95° C. for 5 min. This cDNA may then be amplified by PCR using 250 ng of primer NE1 (5'-TCATTGACAGTCCAGCT-3') (SEQ ID NO:2) in a reaction mixture (100 µl) containing the same buffer as above with 0.25 mM of each dNTP and 2.5 U of Amplitaq DNA polymerase, using about 30 cycles of 94° C. for 1 min., 45° C. for 1 min, and 72° C. for 2 min, to generate a 768 bp region of the HIV pol gene.

5.2 PCR ASSAY OF PERIPHERAL BLOOD MONONUCLEAR CELLS

Peripheral blood mononuclear cells (PBMCs) may be used fresh or following cryopreservation (e.g. at −190° C.). DNA may be prepared from PBMCs using standard techniques for use in detection of HIV proviral DNA. Any suitable HIV primer oligonucleotide(s) may be used in PCR to detect HIV provirus.

In a preferred, nonlimiting embodiment of the invention, cryopreserved (−190° C.) PBMC may be treated with a lysis buffer (for example, 0.45 percent Tween-20, 10 mM Tris HCl pH 8.0, 2.5 mM MgCl$_2$, 50 mM KCl, and 0.1 mg/ml proteinase K) for about two hours at 56° C. and then heat inactivated at 95° C. for 10 minutes. Approximately 1 µg of DNA (20 µl of the PBMC lysate) may be used in the initial PCR amplification with primers A (5'-TTCCCATTAGTCCTATT-3') (SEQ ID NO:1) and NE1 (5'-TCATTGACAGTCCAGCT-3') (SEQ ID NO:2) with reaction conditions as set forth in Larder et al., 1991, AIDS 5:137–144 to generate a 768 bp region of the HIV pol gene.

5.3 PCR ASSAY FOR MUTATION AT CODON 215 OF HIV REVERSE TRANSCRIPTASE

To analyse the changes in codon 215 of the HIV pol gene, a "double" or "nested" PCR procedure was performed using the primers, reagents, and reaction conditions described by Larder et al., 1991, AIDS 5:137–144. Five µl of the 768 bp product generated by PCR with primers A (5'-TTCCCATTAGTCCTATT-3') (SEQ ID NO:1) and NE1 (5'-TCATTGACAGTCCAGCT-3') (SEQ ID NO:2) and either plasma HIV RNA or PBMC DNA may be used in a second series of nested PCR amplifications using primers that detect wild-type sequence or sequence mutated at codon 215. In preferred, non-limiting embodiments of the invention, the following primers may be used: to detect wild-type sequence primers B (5'-GGATGGAAAGGATCACC-3') (SEQ ID NO:3) and 3W (3'-TGGTGTGGTCTGTTTTTGTA-5') (SEQ ID NO:4) and to detect mutants at codon 215, primers B (supra) and 3M (3'-AAGTGTGGTCTGTTTTTGTA-5') (SEQ ID NO:5). PCR may then be performed as follows. About 1 µl of template may be used per PCR reaction in 100 µl containing 25 mM KCl, 50 mM Tris HCl pH 8.3, 0.1 mg/ml bovine serum albumin (BSA), 0.2 mM each of dATP, dGTP, dCTP and dTTP, 0.25 µl of each oligonucleotide primer, and 1.5 mM MgCl$_2$. Reaction mixtures may be heated at 100° C. for two minutes prior to addition of Taq DNA polymerase (2.5 U, Perkin-Elmer Cetus, Connecticut), overlaid with 100 µl of light mineral oil, and subjected to 30 cycles consisting of a denaturation step (1 minute, 94° C.), primer annealing (30 seconds, 45° C.) and DNA synthesis (30 seconds, 72° C.) using, for example, a Perkin Elmer Cetus DNA thermal cycler. Ten µl of PCR product from each set of "nested" PCR reactions may then be analyzed to determine the presence and intensity of the products. For example, PCR reactions may be analyzed on a 3.0 percent agarose gel with ethidium bromide staining; a portion of a patient sample subjected to "nested" PCR using primers B and 3 W may be run in a lane next to another portion of the same patient sample subjected to "nested" PCR using primers B and 3M. A 210 bp PCR product would be expected; if the patient sample contained HIV RT having the codon 215 mutation, the lane carrying primer B/3M PCR product should exhibit a band that is more intense than any corresponding band in the primer B/3 W lane. If the patient sample contained only wild type HIV RT, the band in the primer B/3 W lane should be more intense than any corresponding band in the primer B/3M lane. Alternatively, if the patient sample contained a mixture of wild type and mutant HIV RT, bands of similar intensities should be in both lanes.

5.4 UTILITY OF THE INVENTION

The present invention relates to methods of monitoring, via PCR, the clinical progression of HIV infection in patients receiving antiretroviral therapy. Techniques described in Sections 5.1 through 5.3 supra, may be used as set forth below.

In one particular embodiment, the present invention provides for a method of evaluating the effectiveness of antiretroviral therapy of a patient comprising (i) collecting a plasma sample from an HIV-infected patient who is being treated with an antiretroviral agent; (ii) amplifying the HIV-encoding nucleic acid in the plasma sample using HIV primers in about 30 cycles of PCR; and (iii) testing for the presence of HIV sequence in the product of the PCR; in which the absence of detectable HIV sequence correlates positively with the conclusion that the antiretroviral agent is therapeutically effective and the presence of detectable HIV sequence correlates positively with the conclusion that the antiretroviral agent is therapeutically ineffective. In further, related, embodiments, the presence of detectable HIV sequence correlates positively with an absolute CD4 count of less than 200 cells/mm$^3$, and the absence of detectable HIV sequence correlates positively with a CD4 count greater than 200 cells/mm$^3$. The phrase "correlates positively," as used herein, indicates that a particular result renders a particular conclusion more likely than other conclusions.

In another particular embodiment, the present invention provides for a method of evaluating the effectiveness of antiretroviral therapy of a patient comprising (i) collecting a plasma sample from an HIV-infected patient who is being treated with an antiretroviral agent; (ii) amplifying the HIV-encoding nucleic acid in the plasma sample using HIV primers in about 30 cycles of PCR; and (iii) measuring the HIV RNA copy number using the product of the PCR, in which an HIV RNA copy number greater than about 500 correlates positively with the conclusion that the antiretroviral agent is therapeutically ineffective, and an HIV RNA copy number less than about 200 correlates positively with the conclusion that the antiretroviral agent is therapeutically effective.

In a further embodiment, the present invention provides for a method of evaluating the effectiveness of antiretroviral therapy of a patient comprising (i) collecting one pre-treatment plasma sample from an HIV-infected patient who is about to be treated with an antiretroviral agent; (ii) collecting a post-treatment plasma sample from the HIV-infected patient after the patient has been treated with the antiretroviral agent; (iii) amplifying the HIV-encoding nucleic acid in the pre-treatment and post-treatment plasma samples using HIV primers in about 30 cycles of PCR; (iv) measuring the HIV RNA copy number using the products of the PCRs of step (iii); and (v) comparing the HIV RNA copy number in pre-treatment and post-treatment plasma samples, in which a ratio of HIV RNA copy number in pre-treatment and post-treatment plasma samples of greater than about 4 to 1 correlates positively with the conclusion that the antiretroviral agent is therapeutically effective.

In additional embodiments of the invention, PCR assay may be used to detect mutations at codon 215 of HIV RT which correlate with resistance to antiretroviral therapy and which precede immunologic decline by 6–12 months. Accordingly, the present invention provides for a method of evaluating the effectiveness of antiretroviral therapy of a patient comprising (i) collecting a plasma sample from an HIV-infected patient who is being treated with an antiretroviral agent; and (ii) determining (for example, using "nested" PCR) whether the plasma sample comprises nucleic acid encoding HIV RT having a mutation at codon 215, in which the presence of the mutation correlates positively with immunologic decline of the patient within a six to twelve month period. Under such circumstances, the HIV virus infecting the patient has become, via the mutation, resistant to the antiretroviral agent. It therefore maybe desirable after detecting the mutation,to either increase the dosage of antiretroviral agent, change to another antiretroviral agent, or add one or more additional antiretroviral agents to the patient's therapeutic regimen. For example, if the patient was being treated with zidovudine (AZT) when the mutation arose, the patient's therapeutic regimen may desirably be altered, within about a six to twelve month period of the mutation's occurrence, by either (i) changing to a different antiretroviral agent, such as dideoxyinosine (ddI) and stopping AZT treatment; or (ii) increasing the dosage of AZT; or (iii) adding another antiretroviral agent, such as ddI,to the patient's therapeutic regimen. The effectiveness of the modification in therapy may be evaluated, as set forth above, by monitoring the HIV RNA copy number. A decrease in HIV RNA copy number correlates positively with the effectiveness of a treatment regimen.

Because the mutation at the 215 codon appears first in plasma HIV RNA and later in PBMC proviral DNA, once the mutation is detected in proviral DNA, the treatment regimen is desirably modified with haste in order to avoid immune decline. Accordingly, the present invention provides for a method of evaluating the effectiveness of antiretroviral therapy of a patient comprising (i) collecting PBMC from an HIV-infected patient who is being treated with an antiretroviral agent; and (ii) determining whether the PBMC comprise proviral HIV DNA which comprises a mutation at codon 215, in which the presence of the mutation correlates positively with immunologic decline of the patient within a 4–11 month period (because, as discussed in Section 7, infra, a mutation in serum HIV RNA was found to precede the mutation in proviral DNA by 1–8 months). Once the mutation is detected in proviral DNA, immune decline becomes even more imminent, and alteration of the patient's therapeutic regimen is desirable.

When immune decline is heralded by the increase in HIV RNA copy number and/or the presence of the mutation at codon 215, in addition to altering the patient's antiretroviral therapy, it may also be desirable to treat the patient prophylactically for opportunistic infections, using antifungal, antibiotic, and/or antiparasitic medications.

Antiretroviral agent, as used herein, includes any known antiretroviral agent including, but not limited to, dideoxynucleosides. In preferred embodiments of the invention the antiretroviral agent is AZT. Resistance to certain antiretroviral agents, including AZT, is associated with a mutation at codon 215. Resistance to other antiretroviral agents, such as ddI, is associated with a mutation at codon 74 (74) The present invention provides for analogous techniques in which the effectiveness of antiretroviral therapy is monitored by determining whether plasma HIV RNA or PBMC contain a mutation at codon 74 of HIV RT, in which a mutation at that locus may augur immunological decline and may warrant a modification of antiretroviral therapy.

One preferred, non-limiting, specific embodiment of the invention is as follows: A method of evaluating the effectiveness of AZT therapy of a patient comprising (i) collecting a plasma sample from an HIV-infected patient who is being treated with AZT; (ii) amplifying the HIV-encoding RNA in the plasma sample by converting the RNA to cDNA and amplifying HIV sequences using HIV primers in about 30 cycles of PCR; and (iii) testing for the presence of HIV sequence in the product of the PCR, in which the absence of detectable HIV sequence correlates positively with the conclusion that AZT is therapeutically effective and the presence of detectable HIV sequence correlates positively with the conclusion that AZT is therapeutically ineffective. In most preferred embodiments, the HIV primers used comprise NE1 (supra), SK38 and/or SK39 (supra), and/or the presence of HIV sequence is detected using an enzyme-linked assay (e.g., a horseradish peroxidase based assay). Similar embodiments in which the HIV copy number is measured are also provided for.

Another preferred, non-limiting, specific embodiment of the invention is as follows: A method of evaluating the effectiveness of AZT therapy of a patient comprising (i) collecting a plasma sample from an HIV-infected patient who is being treated with AZT; (ii) amplifying the HIV-encoding RNA in the plasma sample by converting the RNA to cDNA and amplifying HIV sequences using HIV primers that result in a PCR product that comprises that portion of the RT gene that contains the 215 codon (e.g. primer NE1, supra); (iii) performing "nested" PCR using primers that result in PCR products that reflect the presence of wild type (e.g. primers B and 3 W, supra) or 215 codon mutant (e.g. primers B and 3M, supra); and (iv) determining, via the products of "nested" PCR, the presence or absence of a mutation at codon 215 of the HIV RT, in which the presence of the mutation correlates positively with immunologic decline of the patient within a six to twelve month period. An analogous method may be used in which the patient sample is PBMC, and the presence of a mutation is proviral DNA is determined.

6. EXAMPLE: REDUCTION IN PLASMA HUMAN IMMUNODEFICIENCY VIRUS RIBONUCLEIC ACID AFTER DIDEOXYNUCLEOSIDE THERAPY AS DETERMINED BY THE POLYMERASE CHAIN REACTION

6.1 MATERIALS AND METHODS

6.1.1 PATIENTS

After informed consent was obtained, whole blood samples were collected by venipuncture in the presence of acid-citrate-dextrose as an anticoagulant. A 0 single plasma sample was collected from 39 HIV antibody-positive subjects who were not receiving antiretroviral therapy at the time of collection and from 33 HIV antibody-positive subjects who were currently on and had received AZT for a minimum of 3 mo.

Two plasma samples were collected from an additional 27 subjects before and 1 month after initiation of dideoxynucleoside therapy. 18 of these subjects received 500 mg/d of AZT orally. Seven subjects received a combination of zidovudine (150–600 mg/d) and 2',3'-dideoxyinosine (ddI) (134–500 mg/d). Two patients received 500 mg/d of ddI alone (see Table I for individual subject characteristics). Finally, nine of these subjects had two plasma samples taken 1–3 wk. before initiating antiretroviral therapy and two plasma samples taken 1 and 2 mo. after commencing therapy. Plasma was separated within 4 h. by centrifugation at 500 g for 10 min. A second centrifugation was performed on the plasma at 500 g for 30 min. to remove any cellular material. 200 µl of plasma was then mixed with 200 µl of a solution containing 5 M guanidinium thiocyanate, vortexed briefly, and stored at −70° C. until further use. All samples were assayed within 3 mo. of collection. To decrease variance, all specimens to be compared from the same subject were run in the same assay.

6.1.2 EXTRACTION OF RNA FROM PLASMA

RNA was extracted from plasma by the method described in Chomczynski et al., 1987, Ann. Biochem. 162:156–159. Briefly, 200 µl of clarified plasma to which 200 µl of 5 M guanidinium thiocyanate had previously been added was extracted with phenol/chloroform and precipitated with isopropanol. The resulting pellet was then washed in 75% ethanol, dried, and brought up in diethylpyrocarbonate treated, glass distilled water.

6.1.3 REVERSE TRANSCRIPTION AND AMPLIFICATION OF cDNA

HIV RNA was transcribed to cDNA using Moloney murine leukemia virus reverse transcriptase (Bethesda Research Laboratories, Gaithersburg, Md.) by the method described in Kawasaki, 1990, "In PCR Protocols: A Guide to Methods and Applications" pp. 21–27, M.A. Innis, D. H. Gelfand, J. J. Sninsky, and T. J. White, eds. Academic Press, Berkeley, Calif.. Oligomers used for amplification included SK38, SK39, and SK19 (Kellog et al., 1990, "In PCR Protocols: A Guide to Methods and Applications," pp. 337–348, M. A. Innis, D. H. Gelfand, J. J. Sninsky, and T. J. White, eds. Academic Press, Berkeley, Calif.). Biotinylation of SK38 and horseradish peroxidase (HRP) labeling of probe SK19 were prepared as described in Levenson et al., 1990, "In PCR Protocols: A Guide to Methods and Applications," pp. 99–112 M. S. Innis, D. H. Gelfand, J. J. Sninsky, and T. J. White, eds. Academic Press, Berkeley, Calif. Amplification of HIV cDNA was carried out as follows: to a 100-µl reaction mixture was added the cDNA, 50 pmol of primers SK38 and SDK39, 10 mM of each dNTP, 10 mM Tris (pH 8.3), 2.5 mM $MgCl_2$, 50 mM KCl and 2.5 U of recombiTaq DNA polymerase (Perkin-Elmer Cetus, Norwalk, Conn.). The mixture was then overlaid with 50 µl of mineral oil. Tubes were placed in a DNA thermal cycler (Perkin-Elmer Cetus) for 30 cycles of amplification with the following program: 95° C./30 s, 55° C./30s, and 72° C./60 s for denaturation, annealing, and extension, respectively. Negative and positive controls which included both high and low copy number HIV RNA and DNA were added at each step.

6.1.4 ENZYME-LINKED AFFINITY ASSAY

To detect and quantitate PCR product, 96-well microplates (Maxisorp; Nunc, Naperville, Ill.) were coated with 100 µl of a 0.1 mg/ml solution of avidin (Sigma Chemical Co., St. Louis, Mo.) in 50 mM $Na_2CO_3$ (pH 9.6) overnight at room temperature. Wells were then washed twice with PBS. Wells were then filled with 300 µl of a blocking solution containing 5× Denhardt's solution, 1% gelatin (Sigma), 250 µl/ml sheared herring sperm DNA (Promega Biotec, Madison, Wis.) at least overnight at 4° C. Immediately before use, the blocking solution was aspirated from each well and 5 µl PCR product and 65 µl of a hybridization solution, containing 5× saline sodium phosphate EDTA, 5× Denhardt's solution, and 1 pmol of HRP-labeled SK19 HIV gag specific probe was added to each well. A capture and hybridization reaction was then carried out in the well for 1 h. at 42° C. The 96-well microplate was then placed in a Biomek™ 100 Automated Workstation (Beckman Instruments, Inc., Palo Alto, Calif.) where wells were washed 20 times with BPS containing 0.05% Tween-20. The HRP substrate 0-phenylenediamine (Sigma) was prepared at 0.6 mg/ml in 0.1 M citrate buffer (pH 5.5) containing 0.03% hydrogen peroxide. 150 µl of this substrate solution was added to each well. After 10 min. the reaction was stopped with 1N $H_2SO_4$ and the optical density of each well measured at 490 nm by the Biomek 1000. A lower level of positivity had been defined as an absorbance of 0.135. This cutoff value was calculated from the mean absorbance obtained from a group of seronegative samples plus three standard deviations. Copy number from subject samples were determined from the absorbances obtained from a dilution series of an RNA gag gene construct of known copy number described in Holodniy et al., 1991, J. Infect. Dis. 163:862–866. The lower level of sensitivity in this assay was 40 copies of HIV gag gene RNA.

6.1.5 PLASMA HIV CULTURE AND P24 ANTIGEN ASSAY

Quantitative HIV plasma microculture was performed according to the method described in Ho et al., 1989, N. Engl. J. Med. 321:1621–1625. P24 antigen was detected by an antigen capture assay by a method provided by the supplier (Abbott Laboratories, North Chicago, Ill.).

6.1.6 STATISTICAL ANALYSIS

Sample optical density was converted to copy number and analyses performed on samples expressed as RNA copy number/200 μl of plasma. A t test of independent samples was used in analysis of subject who did not receive antiretroviral therapy compared to subjects who were receiving AZT. A t test of paired samples was used to analyze paired plasma data and CD4 counts from subjects pre- and post-therapy. All t tests were two tailed. A Fisher's exact test or chi square test were used for analysis of proportion where appropriate. Statistical significance was defined as $P<0.05$.

6.2 RESULTS 72 subjects were evaluated in a cross-sectional study of HIV disease to determine plasma HIV RNA copy number by PCR. The results are presented in FIG. 1. 39 subjects who were not currently receiving antiretroviral therapy and 33 subjects who were receiving AZT were evaluated. Untreated subjects were more likely to have a positive signal than treated subjects (32 of 39 vs. 16 of 33, respectively, P 0.008. chi square). In the 39 subjects who were not currently receiving therapy, the mean plasma HIV RNA copy number was 690±360 (mean±SEM) per 200 μl of plasma, while the 33 subjects who had been receiving AZT therapy had a mean copy number of 134±219 (P <0.05). Mean CD4 count for each group was 316±45 and 300±37, respectively (P=NS).

Subgroups were then analyzed with respect to CD4 count. Among those with<200 CD4 cells, untreated subjects were more likely to have positive signal than treated subjects (18 of 19 vs. 9 of 14, P<0.04, Fisher's exact test). Among those with>200 CD4 cells, 14 of 20 untreated subjects vs. 7 of 19 treated subjects had a detectable signal (P=NS, Fisher's exact test). Untreated subjects with CD4 count<200/mm$^3$ had a mean RNA copy number of 1,369±707 and mean CD4 count of 73±17; untreated subjects with CD4>200/mm$^3$ had a mean RNA copy number of 44±10 and mean CD4 count of 547±45; treated subjects with CD4 counts <200/mm$^3$ had a mean RNA copy number of 295±5 and mean CD4 count of 115±13; and treated subjects with CD4 counts>200/mm$^3$ had calculated mean RNA copy number of 16±5 (which is below the level of detection of this assay and would be interpreted as negative) and mean CD4 count of 437±41.

27 additional subjects were then evaluated before and 1 mo after initiation of dideoxynucleoside therapy. Clinical parameters of the subjects are presented in Table I. PCR results are presented in FIG. 2. Results show that plasma HIV RNA copy number fell from 540±175 to 77±after therapy (P<0.05, paired t test). Mean CD4 count increased from 399±24 to 442±25 after 4 wk of therapy (P<0.006, paired t test).

TABLE 1

Clinical Parameters and PCR Analysis of Plasma HIV RNA from 27 Patients

| Patient No. | Antiviral treatment | Pre/post CD4 | Pre/post HIV RNA |
|---|---|---|---|
| 1* | AZT‡ | 647/561 | 106/90 |
| 2* | AZT | 541/651 | 130/0 |
| 3 | AZT | 840/874 | 550/0 |
| 4 | AZT | 432/462 | 100/77 |
| 5* | AZT | 379/415 | 87/57 |
| 6* | AZT | 428/408 | 40/42 |
| 7 | AZT | 422/345 | 94/94 |
| 8 | AZT | 420/402 | 0/0 |
| 9 | AZT | 432/532 | 93/65 |
| 10 | AZT | 430/430 | 105/52 |
| 11 | AZT | 429/404 | 123/50 |
| 12 | ddI + AZT§ | 280/220 | 526/0 |
| 13 | AZT | 323/320 | 78/45 |
| 14 | AZT | 320/456 | 95/95 |
| 15 | AZT | 353/387 | 301/0 |
| 16 | ddI + AZT§ | 309/399 | 300/0 |
| 17 | ddI + AZT§ | 337/398 | 260/0 |
| 18 | ddI‖ | 328/310 | 966/0 |
| 19 | ddI + AZT¶ | 383/491 | 245/0 |
| 20 | AZT | 404/413 | 0/0 |
| 21 | AZT | 270/450 | 958/72 |
| 22 | ddI + AZT¶ | 292/344 | 60/0 |
| 23 | AZT | 320/295 | 2769/437 |
| 24 | ddi‖ | 222/370 | 3944/0 |
| 25 | AZT | 568/732 | 2014/925 |
| 26 | DDI + AZT** | 367/473 | 217/0 |
| 27 | DDI + AZT** | 310/399 | 439/0 |

*Remote history of AZT use.
"AZT dose 500 mg/d unless otherwise stated.
§AZT 300 mg/d + ddI 334 mg/d.
‖ddi 500 mg/d.
¶600 mg/d + ddI 500 mg/d.
**AZT 150 mg/d + ddI 134 mg/d.

Finally, 9 of the 27 subjects had two samples taken before initiation of therapy and two samples taken 1 and 2 months after commencing therapy. The results are presented in FIG. 3. When two pretherapy time points were analyzed for constancy of signal, results show that mean copy number for each pretherapy time point was 945±377 and 643±392.

Two subjects had a second pretherapy sample which was negative. When both pretherapy copy number values were compared to posttherapy values, plasma HIV RNA copy number fell from 794±274 to <40 (which is below the lower level of detection in this assay) after 1 and 2 mo of therapy (P<0.05, paired t test). Mean CD4 count increased from 314±165 to 378±25 (P<0.05, paired t test).

Plasma culture was performed on fresh material obtained from the initial pretreatment sample for 23 of 27 of these patients. Only 7 of 23 were plasma virus positive by culture (from 1 to 100 tissue culture infective does/ml). All 23 of these patients were positive by PCR (>40 copies/200 μl ). In addition, a p24 antigen test was performed on all 27 pretreatment samples. Only 2 of 27 had detectable p24 antigen present (>30 pg/ml).

6.3 DISCUSSION

The results presented here demonstrate that plasma HIV RNA can be detected and quantified by copy number in the majority of patients infected with HIV. In addition, plasma HIV RNA copy number may be used as a marker of circulating HIV viral load to assess treatment effect of antiretroviral compounds including dideoxynucleoside compounds. We initially conducted a survey to determine whether treatment or degree of immunologic impairment, based on CD4 count, affected plasma HIV RNA copy number. Untreated patients as a group had higher copy numbers than treated patients. Untreated patients with <200 CD4 cells/mm$^3$ had a higher mean copy number than patients with >200 CD4 cells/mm$^3$. Likewise, treated patients with <200 CD4 cells/mm$^3$/ had higher copy numbers than patients with >200 CD4 cells/mm$^3$, indicating that patients with more advanced HIV disease have higher circulating copy numbers than asymptomatic patients, and that the antiretroviral benefit seen in patients with higher CD4 counts may be waning.

To assess the short-term impact of antiretroviral therapy on patients, 27 patients were evaluated before and 1 mo after initiation of AZT, ddI, or combination therapy. As CD4 counts increased after 1 mo of therapy, HIV RNA copy number fell significantly. However, the response of individual subjects was variable. 16 of 27 subjects had a marked decrease in copy number and 11 of 27 did not. Because the majority of subjects received AZT alone, it was not possible to assess any differences between AZT, ddI, or combination regimens.

Finally, nine subjects had two baseline time points taken in the 3 wk before treatment, followed by two monthly samples posttreatment. Pretreatment signal was constant in 7 of 9 subjects, and 2 subjects had discordant samples, i.e., one was positive and one was negative. This could be related to real changes in circulating HIV RNA, or introduced during sample collection, handling, or the assay. However, pretherapy and posttherapy samples were run in the same assay and so were subject to all of the same reaction conditions. When sample positivity was considered in relation to therapy, 16 of 18 pretherapy samples had a positive signal vs. 0 of 18 posttherapy samples (P<0.001, chi square) showing suppression of HIV RNA copy number with treatment.

Currently there is no standard method to assess circulating viral load in all HIV-infected patients. Plasma viremia, measured by quantitative microculture, can identify and quantify infectious virus in 50–100% of patients, principally those with advanced stages of HIV disease, low CD4 counts, and p24 antigenemia (Ho et al., 1989, N.Engl. J. Med. 321:1621–1625; Coombs et al., 1989, J. Virol. Methods 26:23–21; Ehrnst et al., 1988, N.Engl. J.Med. 324:961–964). Many patients with >200 CD4 cells/mm$^3$ do not have detectable infectious plasma viremia. This may be due to an absence of circulating infectious virus, virus which is neutralized by specific antibody, or the insensitivity of culture techniques. The results presented here indicate that the majority of patients with >200 CD4 cells/mm$^3$ do not have plasma p24 antigen or infectious virus detectable by culture techniques. In the studies described herein, it appears that virus undetectable by culture methods was detectable by PCR methods.

Attempts have been made to assess HIV viral load in patients by molecular techniques, mainly by quantitative PCR of HIV proviral DNA in circulating mononuclear cells or cell-free virion-associated RNA in plasma. Published data suggest that the number of cells infected with HIV increases with advancing disease and that HIV proviral DNA content increases as well. We and others have shown a decrease in HIV proviral DNA with dideoxynucleoside therapy over time (Aoki et al., 1990, AIDS Res. Hum. Retroviruses 6:1331–1339). This was not the case in another published small series (McElrath et al., 1991, J.Clin. Invest. 87:27–30).

We have shown that HIV RNA could be quantified in serum and that copy number increased with disease progression (Holodniy et al., 1991, J.Infect. Dis. 163:862–866). Plasma HIV RNA has been shown to be present before and after seroconversion with quantitative decreases occurring after seroconversion (Hewlett et al., 1988, J.Clin. Immunoassay 11:161–164). The recent report by Daar et al. (Daar et al., 1991, N.Engl. J.Med. 324:961–964), showed a decrease in both plasma viremia and proviral DNA from PBMC, coinciding with seroconversion after acute infection. In one report, plasma HIV RNA levels fell with passive immunoglobulin therapy, suggesting a therapy-based response in circulating HIV RNA load (Karpas et al., 1990, Proc. Natl. Acad. Sci. USA 87:7613–7617). Ottman and colleagues have been successful in detecting HIV RNA in plasma from 95% of patients evaluated (Ottman et al., 1991, J. Virol. Methods 31:273–284). They also studied a group of patients who were receiving AZT to determine whether there was any therapeutic impact on HIV RNA signal. 24 of 25 patients who were receiving AZT had detectable signal. However, methodological differences in that study vs. the present study may have contributed to the differences noted between them. First, Ottman et al. used an ultracentrifugation step to sediment virus, enhancing virion-associated RNA recovery. Second, 40 cycles of amplification after reverse transcription were performed, which would certainly increase the sensitivity of such an assay to successfully detect HIV RNA in virtually all patients. Although sensitivity is increased with increased cycle number, thus detecting signal in virtually all patients, the ability to show the quantitative changes demonstrated here with 30 cycles of amplification is lost.

We have previously shown in serum that quantitative serum cultures were negative in the majority of patients with >200 CD4 cells/mm$^3$ (Holodniy et al. 1991, J. Infect. Dis. 163:862–866). In the current study, 23 plasma samples were evaluated by culture and PCR. All had detectable plasma HIV RNA by PCR<but only seven were plasma HIV-culture positive. Other published experience comparing plasma HIV culture and PCR of HIV RNA from plasma is lacking. Ottman et al. tested only two patients, both of whom were positive in both assays. Coyle et al. reported that 14 of 20 patients had positive plasma cultures and 12 of 20 patients had detectable HIV RNA in plasma, but no information was given regarding concordance or discordance of samples (Coyle et al., 1990, Clin. Res. 38:778a (Abstr.)).

The type of plasma sample and method of processing and storage were found to be very important. The type of anticoagulant used for sample collection can affect detection of plasma RNA. We have previously shown that plasma collected in the present of herapin does not allow detection of signal because of an inhibitory effect of heparin on gene amplification (Holodniy et al., 1991, J.Clin. Microbiol. 29:676–679). Although Coyle et al. (1990, Clin. Res. 38:778a (Abstr.)) found detectable signal from plasma collected in the presence of herapin, an ultracentrifugation step preceding RNA analysis lead to removal of most of the heparin from the enzyme-mediated assay system. However, no comparison experiments among anticoagulants were performed to demonstrate any attenuation of signal obtained in the presence of heparin.

Because of our concern for RNA degradation during specimen storage and freeze thawing, we decided to store fresh plasma at –70° C. in the presence of guanidinium and process samples within 3 mo of collection. Samples were stored in guanidinium for RNAase inhibition. Preliminary data from our laboratory would suggest that plasma HIV RNA signal decays with time in the absence of this RNA stabilizer.

In summary, we have shown that plasma HIV RNA copy number can be quantitated by PCR and does decrease with dideoxynucleoside therapy. The nonisotopic, microplate-based format presented here makes it possible to process multiple patient samples with replicates in a single amplification and assay run.

7. EXAMPLE: RELATIONSHIP OF A MUTATION IN THE HIV REVERSE TRANSCRIPTASE GENE TO DECLINE IN CD4 LYMPHOCYTE NUMBERS IN LONG TERM AZT RECIPIENTS

7.1 MATERIALS AND METHODS

7.1.1 STUDY POPULATION

Cryopreserved PBMC and serum from 40 participants in AIDS Clinical Trial Group (ACTG) protocols 019 (30 patients) and 016 (10 patients) at Stanford University Medical Center AIDS Clinical Trial Unit were used in this study. Patients at enrollment in these studies were AZT naive, had >200 CD4 cells/µl and had few (016) or no symptoms (019) referable to HIV infection. They were subsequently treated with AZT for 2 to 4 years. The most common dosage was 500 mg per day. Approximately one third of patients received either 1200 mg or 1500 mg per day during the initial part of their therapy, but were changed to 500 mg per day when lower doses were found to be as effective but less toxic than higher doses (Fischl et al., 1990, N. Engl. J. Med. 323:1009–1014; Volberding et al., 1990, N. Engl. J. Med. 322:941–949). All samples were obtained from the patients while they were on the protocols and thus no patient developed an AIDS defining diagnosis.

7.1.2 CD4 CELL COUNTS

CD4 cell counts were obtained approximately every three months on each patient. All counts were performed at Stanford's ACTG-qualified cytofluorometry lab. Samples were stained with monoclonal antibodies to CD3, CD4, and CD8. The absolute CD4 count was calculated by multiplying the percent CD4 by the total lymphocyte count.

7.1.3 PBMC PREPARATION

Cryopreserved (−190° C.) PBMC were treated with a lysis buffer (0.45% Tween-20, 10 mM Tris HCl pH 8.0, 2.5 mM MgCl$_2$, 50 mM KCl and 0.1mg/ml proteinase K) for 2 hours at 56° C. and then heat inactivated at 95° C. for 10 min. Approximately lug of DNA (20µl of the PBMC lysate) was used in the initial PCR amplification with primers A(5'-TTCCCATTAGTCCTATT-3') (SEQ ID NO:1) and NE1 (5'-TCATTGACAGTCCAGCT-3') (SEQ ID NO:2) with reaction conditions as described in Larder et al., 1991, AIDS 5:137–144 to generate a 768bp region of the HIV pol gene.

7.1.4 SERUM HIV RNA PREPARATION

Cryopreserved (−70° C.) serum was thawed and then 350 µl of sera was added to 350 µl of solution D (Chomczynski et al., 1987, Anal. Biochem. 162:156–159) (guanadinium thiocyanate +2-mercaptoethanol) and vortexed. RNA was then extracted with phenol and chloroform and precipitated with ethanol as described in Chomczynski et al., 1987, Anal. Biochem. 162:156–15918. HIV RNA was then reverse transcribed to cDNA by using 500 ng of primer A and 5 units of murine leukemia virus (MuLV) reverse transcriptase (Bethesda Research Labs) in 10 µl of amplification buffer (25 mmol/L KCl, 50 mmol/L Tris HCl Ph 8.3, 0.1 mg/ml bovine serum albumin, 1.45 mmol/L each of dATP, dGTP, dCTP and dTTP, 1.5 mmol/L MgCl$_2$, 2.5 units of RNasin (Promega)) for 10 min at room temperature, then 30 min at 42° C. followed by heat inactivation at 95° C. for 5 min. This cDNA was then amplified by PCR using 250 ng of primer NE1 in a reaction mixture (100 µl) containing the same buffer as above with 0.25 mmol/L of each dNTP and 2.5 units of AmpliTaq DNA polymerase (Perkin-Elmer Cetus). This reaction mixture underwent 30 cycles of 94° C. for 1 min, 45° C. for 1 min and 72° C. for 2 min to generate a 768 bp region of the HIV pol gene.

7.1.5 PCR ANALYSIS OF HIV REVERSE TRANSCRIPTASE GENE

To analyze the changes in codon 215 of the HIV pol gene, a "double" PCR procedure was performed using the primers, reagents, and reaction conditions described in Larder et al., 1991, AIDS 5:137–144. Five µl of the 768 bp product generated by PCR with primers A and NE1 was used in a second series of nested PCR amplifications using primer B and 3 W to determine if a wild type sequence was present, or B and 3M to determine if a mutant sequence was present (primer sequences as set forth supra and in Larder et al., 1991, AIDS 5:137–144). Samples were run with negative, positive and reaction mixture controls. Ten µl of PCR product from each of the second set of PCR reactions were analyzed on a 3.0% agarose gel with ethidium bromide staining. PCR products were considered to have a mutant or wild type sequence by the method described by Boucher et al. (1990, Lancet 336:585–590; 1992, J. Infect. Dis. 165:105–110) and Larder et al., 1991, AIDS 5:137–144: a sample was considered to contain the wild type sequence at codon 215 if amplification with the primers B and 3 W resulted in a 210 bp PCR product of highest intensity; a sample was considered to contain a mutant sequence at codon 215 if amplification with the primers B and 3M resulted in a 210 bp PCR product of highest intensity. The sample was considered to have a mixture of wild type and mutant sequences if amplification occurred with both primers 3M and 3 W resulting in PCR products of similar intensity. If a mixture was detected by PCR then that sample was included in the mutant group in our statistical analysis.

7.1.6 AZT SENSITIVITY ASSAY

Patient PBMC were cocultured with mitogen-stimulated PBMC from healthy HIV-seronegative donors. Supernatants from these cultures were collected and frozen when the HIV P24 antigen concentration exceeded 10,000 pg/ml. 30–100 TCID$_{50}$ (50% tissue culture infectious dose) of virus stock was used to infect one million donor PBMC pretreated with different concentrations of AZT (0.0 uM, 0.005 uM, 0.05 uM, 0.5 uM, 5.0 uM). After 7 days, P24 antigen was measured in the cell free supernatant from the cultures with and without zidovudine. The concentration of AZT required to inhibit P24 production by 90% (IC$_{90}$s) as compared to the drug free cultures was determined by nonlinear regression analysis (Chou et al., 1984, Adv. Enzyme Regulation 22:27–55). In this assay, the IC$_{90}$s from AZT-naive patients ranged from 0.002µM to 0.038µM AZT.

7.1.7 STATISTICAL ANALYSIS

All comparisons between the patients with mutant and wild type strains were performed using the student's t-test. The calculations on the IC$_{90}$s determined by the zidovudine sensitivity assay were performed using the log$_{10}$ transformed $IC_{90}$ (i.e. geometric means were used rather than arithmetic means).

7.2 RESULTS

7.2.1 PCR ANALYSIS OF CODON 215 IN PBMC

Proviral DNA was detected by nested PCR in the PBMC of 38 of 40 patients after a mean 34 month treatment period. The two patients in whom proviral DNA could not be detected had high CD4 counts at the time their PBMC were analyzed (729 and 676 cells/µl). PCR amplification of the PBMC from 17 of 38 patients (45%) yielded a 210 bp product with the mutant primer, indicating the presence of a mutation at codon 215 (Thr to Tyr or Phe). The PBMC from 21 of 38 patients (55%) demonstrated amplification product only with the wild type primer (a 210 bp product) indicating the presence of Thr at codon 215.

The mean length of therapy and starting CD4 counts for the two groups were similar (Table 2). However, the 17 patients with a mutation at codon 215 of HIV RT in PBMC proviral DNA had a 50% decrease in their absolute CD4 count between the time they began therapy (378 cells/µl) and the end of the study (189 cells/µl). The 21 patients with a wild type sequence at codon 215 experienced a mean 11% increase in their absolute CD4 count between the time they began therapy (397 cells/µl) and the end of the study (424 cells/µl). The post-treatment CD4 percentages of the two groups of patients were also significantly different (25% in patients with wild-type sequence vs 14% in patients with a mutation in RT at codon 215) (Table 2). The CD4 counts at each time point for each patient are shown in FIGS. 4A and 4B.

TABLE 2

CORRELATION OF PATIENT CD4 COUNT CHANGES WITH PCR ANALYSIS OF CODON 215 OF HIV REVERSE TRANSCRIPTASE IN PBMC

|  | Wildtype | Mutant | p |
|---|---|---|---|
| Number of patients | 21 | 17 |  |
| Months of AZT | 33 ± 8 | 35 ± 7 | 0.4 |
| Starting CD4 measurements |  |  |  |
| Absolute CD4 (cells/µl) | 397 ± 124 | 378 ± 96 | >0.5 |
| CD4 % | 26 ± 8 | 25 ± 6 | >0.5 |
| CD4 measurements at a time of PCR analysis |  |  |  |
| Absolute CD4 (cells/µl) | 424 ± 210 | 189 ± 98 | <0.0001 |
| CD4 % | 25 ± 9 | 14 ± 6 | 0.0001 |

7.2.2 PCR ANALYSIS OF CODON 215 IN HIV RNA FROM SERUM

Serial PBMC samples from earlier time points were available on 8/40 patients; however, serial serum samples from earlier time points were available on 37/40 patients. In these 37 patients, 135 serum samples were tested for the presence of a codon 215 mutation. In 87% of these samples (117), reverse transcribed cDNA could be detected by PCR. Fifteen of the 18 sera that were negative by PCR had been previously subjected to multiple freeze-thaws and therefore could be falsely negative. As all patients were AZT-naive, they were assumed to be wild type at codon 215 at the start of AZT therapy.

Twenty-six of the 37 patients developed a mutation in their HIV RNA. This included the 16 who were also mutant in their PBMC at the end of the study period (FIGS. $5A_1$–$5A_{16}$), and ten patients who were wild type in their PBMC but mutant in serum HIV RNA at the end of the study period (FIGS. $5B_1$–$5B_{10}$). The time preceding the occurrence of the 215 mutation in their serum ranged from 2 to 44 months of therapy. Among these 26 patients, the mean CD4 count at the start of therapy was 398±139 cells/µl and their mean CD4 count at the time of first detection of a codon 215 mutation in their serum was 444±206 cells/µl. Nineteen of the 26 patients with a codon 215 mutation in their serum had follow-up CD4 counts at least 12 months after the mutation was first detected. In these 19 patients, there was a mean decrease of 100±116 CD4 cells/µul (25% decline) at six months and a mean decrease of 170±121 CD4 cells/µl (40% decline) at 12 months.

The 11 patients who remained wild type in their serum over the entire 34 month period of zidovudine therapy had an increase of 7±92 CD4 cells/µl (2% increase). (FIG. 5C). The mean CD4 count at the start of therapy for the patients who later developed a mutant in their serum was 398±139 cells/µl and this was not significantly different than the starting CD4 counts for those patients who remained wild type (397±115 cells/µl. p>0.5). The average length of therapy for both groups was 34 months.

7.2.3 SERUM VIRUS COMPARED TO PBMC PROVIRUS

At the final evaluation of the 38 patients after a mean 34 months of zidovudine, 11 patients were wild type in both serum and PBMC, 17 were mutant in both serum and PBMC, and 10 patients had a mutation in their serum but remained wild type in their PBMC FIG. 6. Eight of the 17 patients with a mutation in proviral DNA at the end of the study period had at least one PBMC sample available from an earlier time point. In these eight patients, a mutation in serum HIV RNA preceded the mutation in proviral DNA by 1–8 months. The findings in these 8 patients and in the 10 patients who were wild type in their PBMC but mutant in their serum shows that detection of the serum mutation precedes detection of the mutation in PBMC. In no instance, did a mutation in patient's PBMC precede its appearance in serum.

7.2.4 AZT SENSITIVITY RESULTS DETERMINED BY CELL CULTURE

In vitro AZT susceptibility testing was performed on 17 of 38 patients using a different aliquot of the same post-treatment PBMC that were used for the PCR analysis. The geometric mean of the $IC_{90}$s of eight patients with the wild type form at 215 was 0.04 µm AZT (range: 0.02–0.28 µm); the geometric mean $IC_{90}$ of nine patients with a mutation at codon 215 was 0.41 µm AZT (range: 0.03–8.0µM; p=0.002).

7.3 DISCUSSION

As an increasing number of HIV infected individuals are offered early treatment with AZT, the significance of drug resistant virus has become an important question. In the present study we found a strong correlation between the presence of a mutation at codon 215, which is linked to AZT resistance and an accelerated decline in CD4 cell number. The patients we studied all began taking AZT when their CD4 cell numbers were relatively high and before the onset of AIDS. We observed that the 17 patients with a mutation at codon 215 in provital DNA in their PBMC experienced a mean 50% decrease in their CD4 count between the time that they began therapy and the time that their cells were analyzed for mutations. The 21 patients who were wild type at codon 215 in their proviral DNA at the end of treatment experienced a mean 11% increase in their CD4 count during the same time period.

Patient cells were only available during the last year of the study. However, by extracting and reverse transcribing HIV RNA from patient's serum specimens we were able to detect codon 215 mutation at earlier time points. The patients in our study with and without a mutation in serum HIV had similar starting CD4 counts (397±115 vs. 398±139, p>0.5) and similar lengths of therapy (34 months in both groups). Yet we found that those patients who develop a mutation in HIV RNA had a subsequent 40% decline in their CD4 cells over the next 12 months. The patients who remained wild type in their serum had a 2% increase in their CD4 cells over 34 months of therapy.

These results show that genetic changes in the virus which confer drug resistance can be rapidly determined directly form patient PBMC and HIV RNA in patients serum using a nested PCR procedure. By using PCR we were able to detect viral nucleic acid in 90% of PBMC samples and 87% of serum samples. Techniques which require culturing HIV from PBMC or serum may select HIV subpopulations with greater tropism for certain cells (Kusumi et al., 1992, J. Virol. 66:875–885; Meyerhans et al., 1989, Cell 58:901–910). This may complicate the analysis of the clinical significance of AZT resistance detected by phenotypic assays.

Earlier clinical studies focused on AZT resistance in patients with initially low CD4 cell counts or who were at high likelihood of disease progression. Furthermore, these studies tested HIV isolates which had been passaged in culture. In contrast, in this study we did not select patients at high likelihood for disease progression but instead we included all patients who remained on AZT for at least 2 years and who had high CD4 counts at the beginning of the study; codon 215 mutations in serum virus occurred early in treatment. The mean CD4 count at the first appearance of the mutation was higher than the CD4 count at the start of therapy (444 vs. 398 cells/µl). This suggests that mutation of the reverse transcriptase gene is not dependent upon low CD4+T cells. On the other hand, we also found that a large percentage of patients remained wild type at codon 215 and phenotypically sensitive to AZT despite almost 3 years of therapy. This may be because our patients were less advanced in their disease or that by using PCR instead of coculture we were able to include patients whose virus might not have grown in culture. These results also suggest that the PBMC may not be the initial source of mutant virus, as evidenced in 18 of our patients where the serum HIV RNA mutation preceded that in PBMC by many months. The source of the mutant HIV detected in serum may be cells in lymphatic, central nervous system or reticuloendothial sites.

The significance of specific mutations in the RT gene with respect to AZT resistance has been defined in patient isolates as well as through molecular cloning experiments (Larder et al., 1989, Science 246:1155–1158; Larder et al., 1991, AIDS 5:137–144; Kellam et al., 1992, 89:1934–1938; St. Clair et al., 1991, Science 253:1557–1559). Of the four mutations first reported to be associated with AZT resistance (codons 67, 70, 215, 219), the mutation at codon 215 has been shown to be the most commonly occurring and to have the greatest impact on susceptibility. This impact on AZT susceptibility will vary depending on whether or not additional mutations are present (Larder et al., 1989, Science 246:1155–1158; Larder et al., 1991, AIDS 5:137–144; Kellam et al., 1992, 89:1934–1938; St. Clair et al., 1991, Science 253:1557–1559; Richman et al., 1991, J. Infect. Dis. 164:1075–1081; Boucher et al., 1992, J. Infect. Dis. 165:105–110). Recent sequencing studies of clinical isolates suggest that there are additional mutations in the RT gene that may contribute to AZT resistance (Japour et al., 1991, Proc. Natl. Acad. Sci. 88:3092–96; Kellam et al., 1992, Proc. Natl. Acad. Sci. USA 89:1934–1938; St. Clair et al., 1991, Science 253:1557–1559). However, the occurrence of the two consecutive nucleotide changes necessary for the amino acid change at codon 215 may be the most important requirement for the development of resistance (Kellam et al., 1992, Proc. Natl. Acad. Sci. U.S.A. 89:1934–1938; Richman et al., 1991, J. Infect. Dis. 164:1075–1081; Boucher et al., 1992, J. Infect. Dis. 165:105–110). In this study, a subset of 17 patients were tested using a cell culture assay which confirmed that the viruses with a mutation at codon 215 had reduced susceptibility to AZT.

The patients with resistant or sensitive virus in our study had similar CD4 counts at the start of AZT therapy and received AZT for a similar period of time. Therefore, the development of resistance and a mutation at codon 215 could not be attributed to any known pretreatment characteristic. None of our patients developed AIDS during our study period and the patients who developed a mutation in their serum HIV RT did so at a relatively high CD4 count. Thus, advanced stage of HIV disease could not explain why some patients developed a mutation while others did not. Additional characteristics of the patient or virus may explain why one HIV strain develops a mutation and another does not. It has been stated that syncytium-inducing, T-cell tropic isolates in HIV-infected individuals contribute to the CD4 cell decline (Tersmette et al., 1989, Lancet 1:983–985). If an HIV isolate can maintain a high level of replicative events despite the presence of AZT, this virus would have a much greater likelihood of mutation. Treatment with AZT may select both syncytium-inducing and drug resistant virus. Selection of more virulent HIV population under prolonged AZT pressure may explain why some patients experienced a CD4 cell decline in the months after the RT mutation arose.

The present report shows a strong association between the presence of a HIV RT mutation and declining CD4 counts in AZT treated patients. Furthermore, it demonstrates that a HIV mutation known to cause AZT resistance can be detected prior to a decline in CD4 cell number.

Various publications are cited herein that are hereby incorporated by reference in their entirety.

What is claimed is:

1. A method of evaluating the effectiveness of antiretroviral therapy of an HIV-infected patient comprising:

(i) collecting a plasma sample from an HIV-infected patient who is being treated with an antiretroviral agent; and (ii) determining whether the plasma sample comprises nucleic acid encoding HIV reverse transcriptase having a mutation at codon 215, in which the presence of the mutation correlates positively with future immunologic decline of the patient within a six to twelve month period.

2. The method of claim 1 in which the mutation at codon 215 is determined by a method comprising polymerase chain reaction.

3. The method of claim 2 which comprises a "nested" polymerase chain reaction.

4. The method of claim 2 or 3 which utilizes primer B (5'-GGATGGAAAGGATCACC-3') (SEQ ID NO:3).

5. The method of claim 2 or 3 which utilizes primer 3M (3'-AAGTGTGGTCTGTTTTTTGTA-5') (SEQ ID NO:5).

6. A method of evaluating the effectiveness of antiretroviral therapy of an HIV-infected patient comprising:
   (i) collecting PBMC from an HIV-infected patient who is being treated with an antiretroviral agent; and
   (ii) determining whether the PBMC comprise proviral HIV DNA which comprises a mutation at codon 215 of the HIV reverse transcriptase gene, in which the presence of the mutation correlates positively with future immunologic decline of the patient within a 4 to 11 month period.

7. The method of claim 6 in which the mutation at codon 215 is determined by a method comprising polymerase chain reaction.

8. The method of claim 7 which comprises a "nested" polymerase chain reaction.

9. The method of claim 7 or 8 which utilizes primer B (5'-GGATGGAAAGGAATCAACC-3') (SEQ ID NO:3).

10. The method of claim 7 or 8 which utilizes primer 3M (3'-AAGTGTGGTCTGTTTTTTGTA-5') (SEQ ID NO:5).

* * * * *

UNITED STATES PATENT AND TRADEMARK OFFICE
CERTIFICATE OF CORRECTION

PATENT NO. : 5,650,268

DATED : July 22, 1997

INVENTOR(S) : Kozal et al.

It is certified that error appears in the above-identified patent and that said Letters Patent is hereby corrected as shown below:

Column 1, line 12, contract number "Al27666-07" should read -- Al27766-07 --.

Signed and Sealed this

Eighth Day of September, 1998

Attest:

BRUCE LEHMAN

*Attesting Officer*     Commissioner of Patents and Trademarks

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
    ( A ) LENGTH: 17 base pairs
    ( B ) TYPE: nucleic acid
    ( C ) STRANDEDNESS: unknown
    ( D ) TOPOLOGY: unknown ( i i ) MOLECULE TYPE: DNA ( x i ) SEQUENCE DESCRIPTION: SEQ ID NO:1:

TTCCCATTAG TCCTATT    17

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:2:

TCATTGACAG TCCAGCT    17

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:3:

GGATGGAAAG GATCACC    17

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:4:

ATGTTTTTTG TCTGGTGTGG T    21

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:5:

ATGTTTTTTG TCTGGTGTGA A    21